US 8,859,505 B2

(12) United States Patent
Ayesa et al.

(10) Patent No.: US 8,859,505 B2
(45) Date of Patent: *Oct. 14, 2014

(54) CYSTEINE PROTEASE INHIBITORS

(75) Inventors: Susana Ayesa, Huddinge (SE); Urszula Grabowska, Huddinge (SE); Ellen Hewitt, Huddinge (SE); Daniel Jonsson, Huddinge (SE); Bjorn Klasson, Huddinge (SE); Pia Kahnberg, Huddinge (SE); Stina Lundgren, Huddinge (SE); Jan Tejbrant, Heddinge (SE); Daniel Wiktelius, Huddinge (SE)

(73) Assignee: Medivir UK Ltd, Little Chesterford, Essex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/704,441

(22) PCT Filed: Jun. 16, 2011

(86) PCT No.: PCT/IB2011/052613
§ 371 (c)(1),
(2), (4) Date: Mar. 22, 2013

(87) PCT Pub. No.: WO2011/158197
PCT Pub. Date: Dec. 22, 2011

(65) Prior Publication Data
US 2013/0172232 A1  Jul. 4, 2013

(30) Foreign Application Priority Data
Jun. 16, 2010  (SE) ...................... 1050618

(51) Int. Cl.
| C07K 14/81 | (2006.01) |
| C07D 233/60 | (2006.01) |
| C07K 5/065 | (2006.01) |
| C07C 271/22 | (2006.01) |
| C07D 277/56 | (2006.01) |
| A61K 38/55 | (2006.01) |
| C07D 305/08 | (2006.01) |
| C07K 5/062 | (2006.01) |
| C07C 275/18 | (2006.01) |
| C07K 5/078 | (2006.01) |
| C07C 237/22 | (2006.01) |
| C07D 213/81 | (2006.01) |

(52) U.S. Cl.
CPC .......... *C07K 5/06139* (2013.01); *C07D 233/60* (2013.01); *C07K 5/06078* (2013.01); *C07C 271/22* (2013.01); *C07D 277/56* (2013.01); *A61K 38/55* (2013.01); *C07D 305/08* (2013.01); *C07K 5/0606* (2013.01); *C07K 5/06034* (2013.01); *C07C 275/18* (2013.01); *C07C 2101/02* (2013.01); *C07C 2101/08* (2013.01); *C07C 237/22* (2013.01); *C07C 2101/04* (2013.01); *C07D 213/81* (2013.01)
USPC ....... 514/20.2; 514/16.6; 514/16.8; 514/17.9; 514/18.3; 514/21.9; 530/331

(58) Field of Classification Search
None
See application file for complete search history.

(56) References Cited

U.S. PATENT DOCUMENTS

| 2011/0312964 A1* | 12/2011 | Ayesa et al. | ................ 514/236.5 |
| 2012/0283305 A1* | 11/2012 | Ayesa et al. | ................... 514/404 |
| 2012/0309673 A1* | 12/2012 | Ayesa et al. | ................... 514/1.7 |

FOREIGN PATENT DOCUMENTS

| WO | WO-97/40066 A1 | 10/1997 |
| WO | WO-03/020287 A2 | 3/2003 |
| WO | WO-2006/102423 A1 | 9/2006 |
| WO | WO-2009/055467 A2 | 4/2009 |
| WO | WO-2010/070615 A1 | 6/2010 |

OTHER PUBLICATIONS

Chapman, Harold A.; "Endosomal proteases in antigen presentation." Curr. Opin. Immunol. (2006) 18 p. 78-84.*
Matsumoto, Fumi et al; "Cathepsins are required for toll like receptor 9 respnoses." Biochem. Biophys. Res. Comm. (2008) 367 p. 693-699.*

(Continued)

Primary Examiner — James H Alstrum Acevedo
Assistant Examiner — Fred Reynolds
(74) Attorney, Agent, or Firm — Gorman IP Law

(57) ABSTRACT

Compounds of the formula I (I)

wherein
$R^{2a}$ and $R^{2b}$ are independently H, halo, $C_1$-$C_4$alkyl, $C_1$-$C_4$haloalkyl or $C_1$-$C_4$alkoxy, or $R^{2a}$ and $R^{2b}$ together with the carbon atom to which they are attached form a $C_3$-$C_6$cycloalkyl;
$R^3$ is a $C_5$-$C_{10}$ alkyl, optionally substituted with 1-3 substituents independently selected from halo, $C_1$-$C_4$haloalkyl, $C_1$-$C_4$alkoxy, $C_1$-$C_4$haloalkoxy; or
$R^3$ is a $C_2$-$C_4$alkyl chain with at least 2 chloro or 3 fluoro substituents; or
$R^3$ is $C_3$-$C_7$cycloalkylmethyl, optionally substituted with 1-3 substituents independently selected from $C_1$-$C_4$alkyl, halo, $C_1$-$C_4$haloalkyl, $C_1$-$C_4$alkoxy, $C_1$-$C_4$haloalkoxy;
$R^4$ is $C_1$-$C_6$alkyl, $C_1$-$C_6$haloalkyl, $C_1$-$C_6$alkoxy, $C_1$-$C_6$haloalkoxy, $C_1$-$C_6$alkylamino, $C_1$-$C_6$dialkylamino or;
$R^4$ is Het or Carbocyclyl, either of which is optionally substituted with 1-3 substituents $R^4$ is Het, carbocyclyl, $C_1$-$C_6$alkyl, $C_1$-$C_6$haloalkyl, $C_1$-$C_6$alkoxy or $C_1$-$C_6$haloalkoxy;
n is 1, 2 or 3;
for the use in the prophylaxis or treatment of a disorder characterised by inappropriate expression or activation of cathepsin S.

22 Claims, No Drawings

(56) References Cited

OTHER PUBLICATIONS

Poole, Jill A. and Rosenwasser, Lanny J.; "The role of immunoglobulin e and immune inflammation: implications in allergic rhinitis." Curr. Allergy and Asthma Rep (2005) 5 p. 252-258.*

Gauriau, Caroline and Bernard, Jean-Francois; "Pain pathways and parabrachial circuits in the rat." Exp. Physiol. (2002) 87.2 p. 251-258.*

Leeson, Paul D. and Springthorpe, Brian; "The influence of drug like concepts on decision making in medicinal chemistry." Nature Rev. (2007) 6 p. 881-891.*

Walker, Brian et al; "Evaluation of dipeptide alpha-keto-beta-aldehydes as new inhibitors of cathepsin S." Biochem. Biophys. Res. Com. (2000) 275 p. 401-405.*

Leroy, Vincnet and Tharalratnam, Sukanthini; "Cathepsin S inhibitors." Expert Opin. Ther. Patents (2004) 14(3) p. 301-311.*

Form PCT/ISA/210, mailed Dec. 22, 2011, for International Application No. PCT/IB2011/052613.

Form PCT/ISA/237, mailed Nov. 25, 2011, for International Application No. PCT/IB2011/052613.

* cited by examiner

CYSTEINE PROTEASE INHIBITORS

This application is the National Stage Under 35 U.S.C. §371 of PCT International Application No. PCT/IB2011/052613 filed on Jun. 16, 2011, which claims priority under 35 USC §119 of Application No. 1050618-6 filed in Sweden on Jun. 16, 2010. The entire contents of each of which are incorporated by reference.

TECHNICAL FIELD

This invention relates to inhibitors of cathepsin S, and their use in the treatment of disorders involving cathepsin S such as autoimmune disorders, allergy and chronic pain conditions.

BACKGROUND TO THE INVENTION

The papain superfamily of cysteine proteases are widely distributed in diverse species including mammals, invertebrates, protozoa, plants and bacteria. A number of mammalian cathepsin enzymes, including cathepsins B, F, H, K, L, O, S, and W, have been ascribed to this superfamily, and inappropriate regulation of their activity has been implicated in a number of metabolic disorders including arthritis, muscular dystrophy, inflammation, glomerulonephritis and tumour invasion. Pathogenic cathepsin like enzymes include the bacterial gingipains, the malarial falcipains I, II, III et seq and cysteine proteases from *Pneumocystis carinii, Trypanosoma cruzei* and *brucei, Crithidia fusiculata, Schistosoma* spp.

In WO 97/40066, the use of inhibitors against Cathepsin S is described. The inhibition of this enzyme is suggested to prevent or treat disease caused by protease activity. Cathepsin S is a highly active cysteine protease belonging to the papain superfamily. Its primary structure is 57%, 41% and 45% homologous with human cathepsin L and H and the plant cysteine protease papain respectively, although only 31% homologous with cathepsin B. It is found mainly in B cells, dendritic cells and macrophages and this limited occurrence suggests the potential involvement of this enzyme in the pathogenesis of degenerative disease. Moreover, it has been found that destruction of Ii by proteolysis is required for MHC class II molecules to bind antigenic peptides, and for transport of the resulting complex to the cell surface. Furthermore, it has been found that Cathepsin S is essential in B cells for effective Ii proteolysis necessary to render class II molecules competent for binding peptides. Therefore, the inhibition of this enzyme may be useful in modulating class II-restricted immune response (WO 97/40066). Other disorders in which cathepsin S is implicated are asthma, chronic obstructive pulmonary disease, endometriosis and chronic pain.

BRIEF DESCRIPTION OF THE INVENTION

According to a first aspect of the invention there is provided a compound of the formula I:

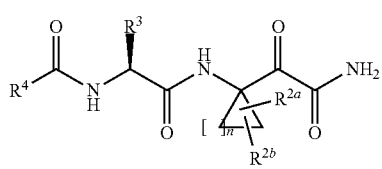

(I)

wherein
$R^{2a}$ and $R^{2b}$ are independently selected from H, halo, $C_1$-$C_4$alkyl, $C_1$-$C_4$haloalkyl, $C_1$-$C_4$alkoxy, or $R^{2a}$ and $R^{2b}$ together with the carbon atom to which they are attached form a $C_3$-$C_6$cycloalkyl;
$R^3$ is a $C_5$-$C_{10}$ alkyl, optionally substituted with 1-3 substituents independently selected from halo, $C_1$-$C_4$haloalkyl, $C_1$-$C_4$alkoxy, $C_1$-$C_4$haloalkoxy; or
$R^3$ is a $C_2$-$C_4$alkyl chain with at least 2 chloro or 3 fluoro substituents; or
$R^3$ is $C_3$-$C_7$cycloalkylmethyl, optionally substituted with 1-3 substituents independently selected from $C_1$-$C_4$alkyl, halo, $C_1$-$C_4$haloalkyl, $C_1$-$C_4$alkoxy, $C_1$-$C_4$haloalkoxy;
$R^4$ is $C_1$-$C_6$alkyl, $C_1$-$C_6$haloalkyl, $C_1$-$C_6$alkoxy, $C_1$-$C_6$haloalkoxy, $C_1$-$C_6$alkylamino, $C_1$-$C_6$dialkylamino or;
$R^4$ is Het or Carbocyclyl, either of which is optionally substituted with 1-3 substituents independently selected from:
halo, azido, cyano, hydroxy, oxo, $C_1$-$C_4$alkyl, $C_1$-$C_4$haloalkyl, $C_1$-$C_4$alkoxy, $C_1$-$C_4$haloalkoxy, $C_1$-$C_4$alkoxycarbonyl, $C_1$-$C_4$alkylcarbonyl, $C_1$-$C_4$alkylsulfonyl, $C_1$-$C_4$alkylsulfonylamino, aminosulphonyl, NRaRb, C(=O)NRaRb, NRaC(=O)Rb, NRaC(=O)ORb, NRa(C=O)NRaRb, wherein oxo as substituent may be present only where valence so permits;
and/or wherein in the Het or Carbocyclyl group is optionally substituted with a group of the formula —X—$R^5$; wherein
X is $C_1$-$C_4$alkylene or a 1-4 membered linkage comprising 0-3 methylene groups disposed adjacent to, or on either side of a —CH(CH$_3$)—, —C(CH$_3$)$_2$—, CF$_2$—, —O—, —CH=CH—, —C≡C—, —NRa—, —C(=O)NRa—, —NRaC(=O)—, —C(=O)NRa—, —NRaS(=O)$_2$—, —S(=O)$_2$NRa—, ester, urea or carbamate function;
$R^5$ is H, $C_1$-$C_4$alkyl or a monocyclic ring selected from $C_3$-$C_6$cycloalkyl, $C_3$-$C_6$cycloalkenyl, phenyl, pyrrolidinyl, piperidinyl, morpholinyl, thiomorpholinyl, piperazinyl, indolinyl, pyranyl, tetrahydropyranyl, tetrahydrothiopyranyl, thiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyridazinyl, tetrazolyl, pyrazolyl, indolyl, the $C_1$-$C_4$alkyl or monocyclic ring being optionally substituted with one to three substituents selected from:
halo, azido, cyano, hydroxy, $C_1$-$C_4$alkyl, $C_1$-$C_4$haloalkyl, $C_1$-$C_4$alkoxy, $C_1$-$C_4$haloalkoxy, $C_1$-$C_4$alkoxycarbonyl, $C_1$-$C_4$alkylcarbonyl, amino, $C_1$-$C_4$alkylamino, $C_1$-$C_4$dialkylamino, $C_1$-$C_4$alkylsulfonyl, $C_1$-$C_4$alkylsulfonylamino, aminocarbonyl, aminosulphonyl;
n is 1, 2 or 3;
Ra and Rb are independently H, $C_1$-$C_4$alkyl;
Het is a stable, monocyclic or bicyclic, saturated, partially saturated or aromatic ring system containing 1-4 heteroatoms independently selected from O, S and N, each ring having 5 or 6 ring atoms;
Carbocyclyl is $C_3$-$C_6$cycloalkyl, $C_5$-$C_6$cycloalkenyl or phenyl;
or a pharmaceutically acceptable salt, hydrate or N-oxide thereof.

Typical embodiments of the invention include compounds wherein n is 1 or 2, i.e. compounds having a 1,1-cyclopropylenyl or 1,1-cyclobutylenyl ring, thus providing compounds according to formula Ia or Ib respectively.

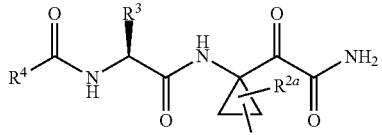

(Ia)

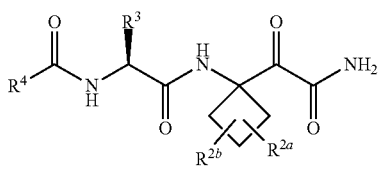

(Ib)

The substituents $R^{2a}$ and $R^{2b}$ may be attached to any of the atoms of the 1,1-cycloalkylenyl group.

In some embodiments of the invention the 1,1-cycloalkylenyl ring is unsubstituted, i.e. $R^{2a}$ and $R^{2b}$ are both H.

In some embodiments of the invention where n is 2, the 1,1-cyclobutylenyl ring is substituted with one or two substituents, i.e. one or both of $R^{2a}$ and $R^{2b}$ is/are not H. Typically according to these embodiments, the substituent(s) is/are located in the 2-position of the cyclobutylenyl ring, thus providing compounds according to formula Ic:

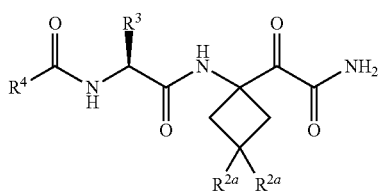

(Ic)

In some embodiments where n is 2, $R^{2a}$ and $R^{2b}$ are both hydrogen. In alternative embodiments where n is 2, one of $R^{2a}$ and $R^{2b}$ is H and the other is halo, $C_1$-$C_4$alkyl, $C_1$-$C_4$haloalkyl or $C_1$-$C_4$alkoxy. In further alternative embodiments where n is 2, $R^{2a}$ and $R^{2b}$ are both halo, $C_1$-$C_4$alkyl or $C_1$-$C_4$haloalkyl.

Typical embodiments where n is 2, include compounds wherein one of $R^{2a}$ and $R^{2b}$ is H, and the other is Cl, F, $CF_3$ or MeO.

In a preferred embodiment where n is 2, one of $R^{2a}$ and $R^{2b}$ is H, and the other is F. Specially preferred according to this embodiment are compounds having the stereochemistry shown in formula Id:

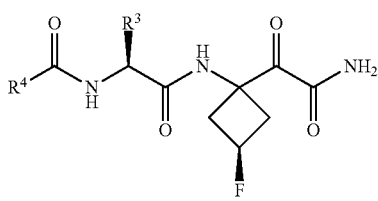

(Id)

In some embodiments where n is 2, $R^{2a}$ and $R^{2b}$ are both F. Compounds of this aspect have the formula Ie:

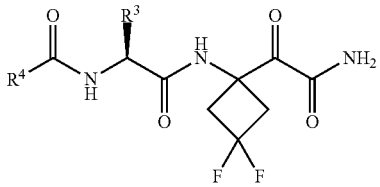

(Ie)

In other embodiments where n is 2, one of $R^{2a}$ and $R^{2b}$ is H, and the other is Cl, F, $CF_3$ or MeO.

In some embodiments $R^{2a}$ and $R^{2b}$ together with the carbon atom to which they are attached form a $C_3$-$C_6$cycloalkyl;

In some embodiments $R^3$ is cycloalkylalkyl, optionally substituted, for example with halo, (such as F) or alkoxy (such as MeO). Exemplary species include 1-methylcyclopentylmethyl, 1-methylcyclohexylmethyl, 1-methylcyclobutylmethyl, 1-methyl-3,3-difluorocyclobutylmethyl, 1-methyl-4,4-difluorocyclohexylmethyl, cyclopropylmethyl or 1-methyl-3,3-difluorocyclopentylmethyl.

Representative $R^3$ species include t-butylmethyl, cyclobutylmethyl, 1-methylcyclobutylmethyl and 1-methylcyclopentylmethyl, any of which is optionally substituted with one or two F or MeO. Representative species are 1-fluorocyclobutylmethyl and 1-fluorocyclopentylmethyl.

Further representative $R^3$ species include 1-methylcyclopentylmethyl and 1-fluorocyclopentylmethyl, Other embodiments have $R^3$ as a straight or branched alkyl chain of 5-10 C-atoms, optionally substituted with 1-3 halo, (e.g. Cl or F), or a $C_1$-$C_4$alkoxy (e.g. MeO). Exemplary species include 2,2-dimethylpropyl, 3,3-dimethylpentyl, 2,2,3,3-tetramethylbutyl. Exemplary species of halogenated alkyl include 2,2-dichloroethyl, 3,3,3-trifluoropropyl, 2,2-trifluoromethylethyl, or 2,2,2-trifluoroethyl.

One embodiment of the invention include compounds wherein $R^4$ is $C_1$-$C_6$alkyl, such as ethyl, isopropyl or tert.butyl.

Another embodiment includes compounds wherein $R^4$ is $C_1$-$C_6$haloalkyl, such as chloroalkyl or fluoroalkyl. Typically according to this embodiment, $R^4$ is mono, di or tri fluoro$C_1$-$C_6$alkyl, such as monofluoropropyl, difluoropropyl, trifluoropropyl or trifluorobutyl.

Another embodiment of the invention includes compounds wherein $R^4$ is $C_1$-$C_6$alkoxy or $C_1$-$C_6$haloalkoxy, thus affording compounds having a carbamate function as shown in formula II,

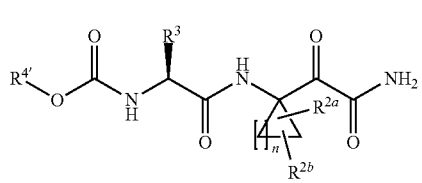

(II)

wherein $R^{4'}$ is $C_1$-$C_6$alkyl or $C_1$-$C_6$haloalkyl. Typically according to this embodiment, $R^{4'}$ is methyl or ethyl.

One embodiment of the invention includes of compounds of formula II, wherein n is 2 and at least one of $R^{2a}$ and $R^{2b}$ is halo, $C_1$-$C_4$alkyl, $C_1$-$C_4$haloalkyl or $C_1$-$C_4$alkoxy. Typically according to this embodiment, one of $R^{2a}$ and $R^{2b}$ is H, and the other is chloro, fluoro, trifluoromethyl or methoxy; especially fluoro or methoxy. Preferably according to this embodiment, $R^{2a}$ and $R^{2b}$ are located in the 2-position of the cyclobutylenyl group.

Preferred embodiments of the invention include compounds of formula II wherein n is 2, one of $R^{2a}$ and $R^{2b}$ is H, and the other is F. Specially preferred according to this embodiment are compounds wherein the F-atom is located in the 2-position of the cyclobutylenyl group, and having the stereochemistry shown in formula IIa:

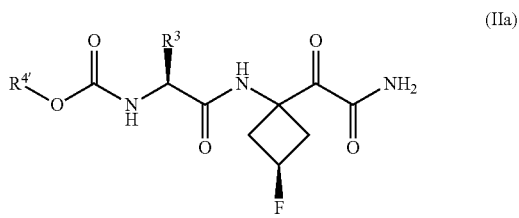

(IIa)

Other embodiments of the invention include compounds of formula II, wherein n is 2, $R^{2a}$ and $R^{2b}$ are both F, thus providing compounds of formula IIb:

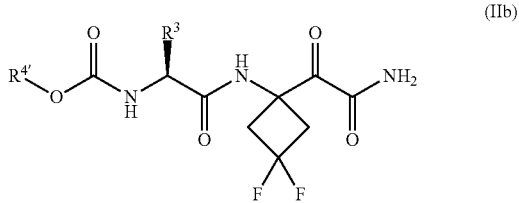

(IIb)

In further embodiments of compounds of formula II, $R^{2a}$ and $R^{2b}$ are both H, thus providing compounds of formula IIc:

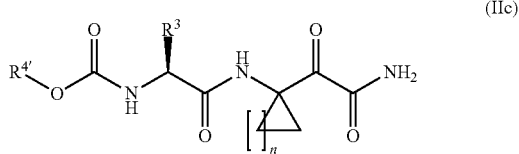

(IIc)

Preferred compounds according to this embodiment are those wherein n is 2, i.e. a cyclobutylenyl group is formed, thus providing compound of the formula IId:

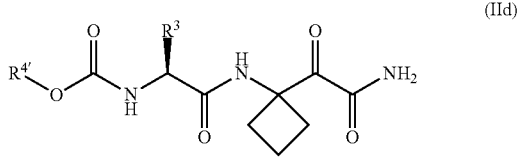

(IId)

In some embodiments, $R^4$ is morpholinyl, piperidinyl, piperazinyl, cyclopentyl, cyclohexyl or pyridinyl, any of which is optionally substituted with halo, hydroxy, $C_1$-$C_4$alkyl, $C_1$-$C_4$haloalkyl, $C_1$-$C_4$alkoxy, $C_1$-$C_4$haloalkoxy, amino, $C_1$-$C_4$alkylamino, di($C_1$-$C_4$-alkyl)amino or $NR^aS(=O)_mRq$;

where $R^a$ is H or $C_1$-$C_4$alkyl;

Rq is $C_1$-$C_4$alkyl, Het or Carbocyclyl, any of which is optionally substituted with $C_1$-$C_4$alkyl, halo, $C_1$-$C_4$haloalkyl, $C_1$-$C_4$ alkoxy; and m is 0, 1 or 2.

In other embodiments $R^4$ is an optionally substituted thiazolyl, such as thiazol-5-yl, optionally substituted with $C_1$-$C_4$ alkyl (e.g. Me) halo (e.g. F) or $C_1$-$C_4$alkoxy (e.g. MeO).

In other embodiments $R^4$ is morpholin-4-yl.

In some embodiments, $R^4$ is linked to the adjacent backbone amide through a ring nitrogen, thereby defining a urea function. A representative species is morpholin-4-yl. A further representative species has the partial structure:

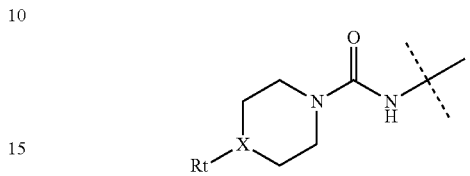

where X is C and Rt is hydroxy, fluoro, $C_1$-$C_4$alkyl, e.g. gem-methyl, $C_1$-$C_4$alkoxy (e.g. MeO) $C_1$-$C_4$haloalkyl (e.g. $CF_3$) or an $NRk$-$S(=O)_2Rs$ function where Rs is $C_1$-$C_4$ alkyl, Het or Carbocyclyl, any of which is optionally substituted with 1-3 $C_1$-$C_4$alkyl (e.g. Me), halo (e.g. F), $C_1$-$C_4$haloalkyl (e.g. $CF_3$), or $C_1$-$C_4$ alkoxy (e.g. MeO). Alternatively X is N and Rt is $C_1$-$C_4$alkyl (e.g. Me) or an —$NRk$-$S(=O)_2Rs$ function where Rs is $C_1$-$C_4$alkyl, Het or Carbocyclyl, any of which is optionally substituted with 1-3 $C_1$-$C_4$alkyl (e.g. Me), halo (e.g. F), $C_1$-$C_4$haloalkyl (e.g. $CF_3$), or $C_1$-$C_4$alkoxy (e.g. MeO).

In some embodiments $R^4$ is piperazin-1-yl or piperidin-1-yl, either of which is substituted at the 4 position or piperidin-4-yl substituted at the 1 position; in each case the substituent is selected from $NHS(=O)_2$Carbocyclyl or $NHS(=O)_2$Het, wherein the Carbocyclyl or Het is optionally substituted with halo, $C_1$-$C_4$alkyl, $C_1$-$C_4$haloalkyl or $C_1$-$C_4$alkyoxy.

In other embodiments, $R^4$ is cyclohexyl or piperazin-1-yl substituted at the 4 position with halo, amino, $C_1$-$C_4$alkylamino di-($C_1$-$C_4$alkyl)amino or hydroxy.

In some embodiments $R^4$ is substituted phenyl.

In some embodiments $R^4$ is phenyl which is substituted with 1, two or three substituents independently selected from halo, hydroxy, $C_1$-$C_4$alkyl, $C_1$-$C_4$haloalkyl, cyano, $C_1$-$C_4$alkylC(=O)NH— and $C_1$-$C_4$alkoxy.

Representative species include phenyl substituted with m-fluoro, p-fluoro, p-hydroxy, p-hydroxy-m-chloro, p-hydroxy-m-fluoro, p-hydroxy-m-methoxy, p-hydroxy-m-methyl, bis-p-chloro-p-hydroxy, m-cyano, p-acetamido or o-fluoro-p-hydroxy.

As defined above, $R^4$ may be substituted with a group of the formula $X$—$R^5$, where $R^5$ is H, optionally substituted $C_1$-$C_4$alkyl or an optionally substituted monocyclic ring which is spaced from the $R^4$ ring by the divalent X linker.

Linker X may comprise a straight chain $C_1$-$C_4$alkylene, such as ethylene or methylene. Alternatively, the linker may comprise a divalent function selected from $CH(CH_3)$, $C(CH_3)_2$, $CF_2$, ethene, ethyne, $C_0$-$C_4$alkylamine, $C_0$-$C_4$alkylamide, sulphonamide, ester, ether, urea or carbamate, which may be bonded direct to $R^4$ and/or $R^5$ or may have one or more methylene groups between the function and $R^4$ and/or between the function and $R^5$. The total length of the linker (including any methylene groups between the function and $R^4$ and/or $R^5$ is 1-4 chain atoms, preferably one to three.

Divalent functions in the X-linker containing multiple hetero atoms, such as amide, sulphonamide, ester or carbamate may be disposed in either orientation, for example —O(C=O)NH— or —NH(=O)O— in the case of a carbamate. The expressions $C_0$-$C_4$alkylamine and $C_0$-$C_4$alkylamide in the context of the X-linker mean that an alkyl group (or H in the case of $C_0$) branches from the nitrogen atom, for example —NH—, —N(CH$_3$)—, —NHC(=O)—, —N(CH$_3$)C(=O), —C(=O)N(CH$_3$)— etc.

Still further R$^4$ groups include those described in WO0664206 the contents of which are incorporated by reference. Notable R$^4$ groups from this reference include those with the partial structures:

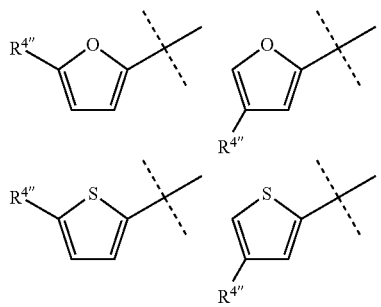

wherein
R$^{4''}$ is H, halo, OC$_1$-C$_4$alkyl, C(=O)NRkRl, NRkC(=O)C$_1$-C$_4$alkyl, NRkC(=O)NRkRl or —NRkC(=O)OC$_1$-C$_4$alkyl, or NHC(=O)OMe, Rk and Rl are independently H, C$_1$-C$_4$alkyl or C(=O)C$_1$-C$_4$alkyl or Rk, Rl and an adjacent N atom to which they are both attached defines a cyclic amine selected from pyrrolidinyl, piperidinyl, morpholinyl, piperazinyl or N-methylpiperazinyl.

Favoured subsets include those wherein R$^{4''}$ is fluoro, methoxy, dimethylcarbamoyl, NHC(=O)Me, —NHC(=O)NHCH$_3$, NHC(=O)N(CH$_3$)$_2$, NHC(=O)OMe or a cyclic amine.

Other R$^4$ embodiments within WO0664206 have the partial structures:

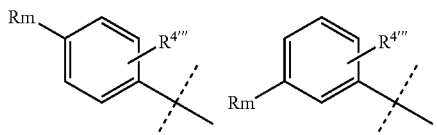

where Rm is —NRaSO$_m$R$^5$ or —NHC(=O)NRkRl;

Rk, Rl and the N atom to which they are both attached defines a cyclic amine selected from pyrrolidinyl, piperidinyl, morpholinyl, piperazinyl or N-methylpiperazinyl;

and R$^{4'''}$ is H, C$_1$-C$_4$alkyl, C$_1$-C$_4$haloalkyl, halo, cyano, hydroxyl or C$_1$-C$_4$alkoxy.

Favoured subsets include those wherein R$^5$ is C$_1$-C$_4$alkyl, such as methyl, ethyl or i-propyl or t-butyl; halogenated C$_1$-C$_4$alkyl such as trifluoromethyl; C$_3$-C$_6$cycloalkyl, such as cyclopropyl or cyclohexyl; or phenyl or benzyl, any of which is optionally substituted with C$_1$-C$_4$alkyl, C$_1$-C$_4$haloalkyl, halo, cyano, C$_1$-C$_4$alkoxy.

Other R$^4$ embodiments within WO0664206 have the partial structures:

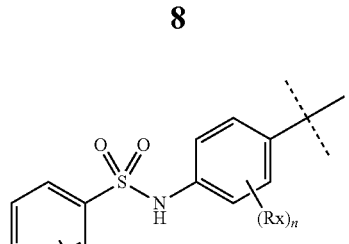

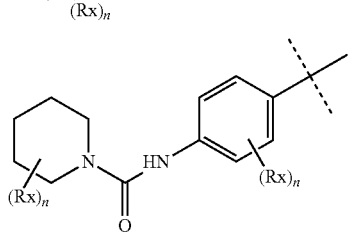

where Rx is independently selected from Me, F, Cl, CF$_3$ and OMe, and n is independently 0, 1 or 2.

A favoured subset has the partial structure:

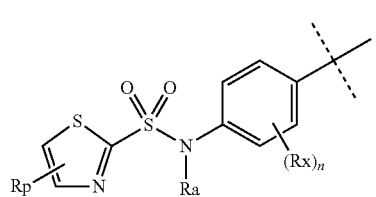

Ra is H or methyl,

Rp is H, Me, F,

Rx is independently selected from Me, F, Cl, CF$_3$ and OMe, and n is 0, 1 or 2;

especially with the partial structure:

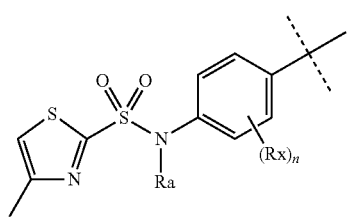

where R$^x$ is H, F, Me.

Still further R$^4$ groups described in WO06/64206 include:

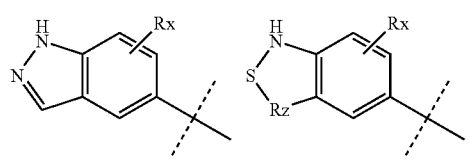

where R$^x$ is H, F, Cl, CF$_3$, Me, OMe, Rz is CH, NH, NMe or O and the S atom is optionally oxidised to

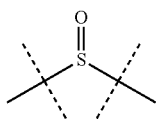

or preferably

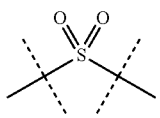

Still further R⁴ groups described in WO06/64206 include:

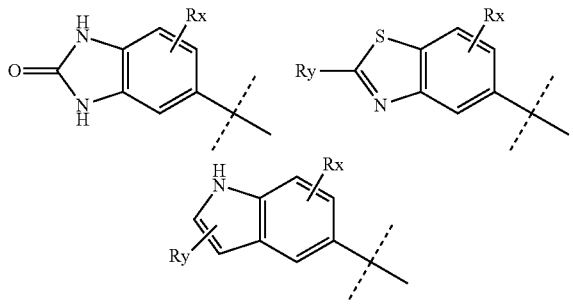

where Ry is H, $C_1$-$C_4$alkyl, amino, NH$C_1$-$C_4$alkyl (such as methylamino), N($C_1$-$C_4$alkyl)$_2$ such as dimethylamino), NHC(=O)$C_1$-$C_4$alkyl (such as acetamido);

ring nitrogens are optionally substituted with $C_1$-$C_4$alkyl (such as methyl, ethyl or t-butyl), or C(=O)$C_1$-$C_4$alkyl (such as acetyl); and Rx is H, F, Cl, CF$_3$, Me, OMe.

Still further R⁴ groups described in WO06/64206 include:

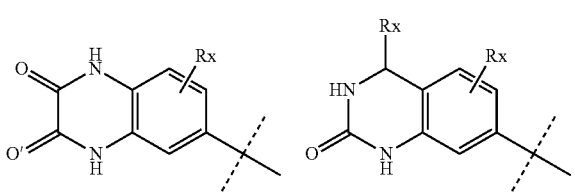

where Rx is independently H, F, Cl CF$_3$ or OMe;

one or both ring nitrogens are optionally substituted with $C_1$-$C_4$alkyl (such as methyl, ethyl or t-butyl), or C(=O) $C_1$-$C_4$ alkyl (such as acetyl);

O' is absent (i.e. 2 hydrogen atoms) or O.

Further typical R⁴ group include:

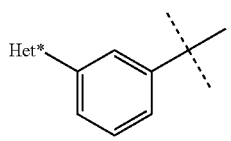

wherein Het* is a 5 or 6-membered, saturated, partially unsaturated or aromatic heterocycle containing 1-3 heteroatoms independently selected from S, O and N.

Preferred compounds of the invention are those having the formula If:

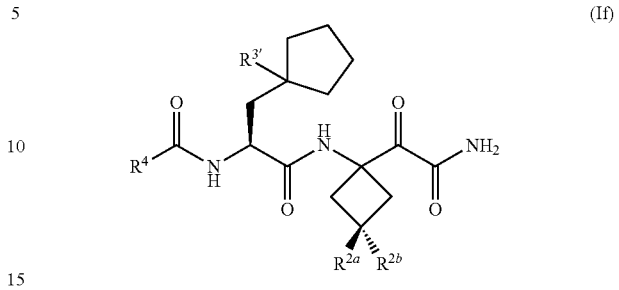

wherein $R^{3'}$ is $CH_3$ or F, $R^{2a}$ and $R^{2b}$ are independently H or F, and $R^4$ is $C_1$-$C_6$alkyl, $C_1$-$C_6$haloalkyl or $C_3$-$C_6$cycloalkyl, wherein $C_3$-$C_6$cycloalkyl is optionally substituted with methyl or $CF_3$.

Further preferred compounds of the invention are those having the formula IIe:

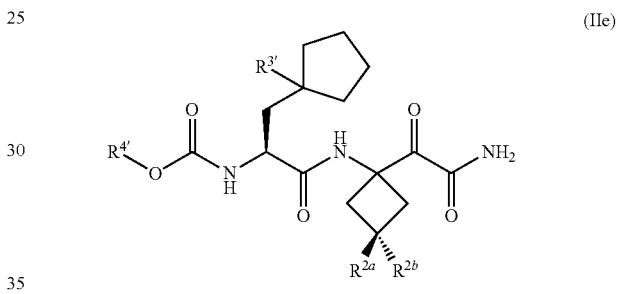

wherein $R^{3'}$ is $CH_3$ or F, $R^{2a}$ and $R^{2b}$ are independently H or F, and $R^{4'}$ is $C_1$-$C_6$alkyl, $C_1$-$C_6$haloalkyl.

The compounds of formula I are characterised by various advantageous pharmaceutical properties and exhibit at least one improved property in view of the compounds of the prior art. In particular, the inhibitors of the present invention are superior in one or more of the following pharmacological related properties, i.e. potency, decreased cytotoxicity, improved pharmacokinetics, acceptable dosage and pill burden.

Without in any way wishing to be bound by theory, or the ascription of tentative binding modes for specific variables, P1, P2 and P3 as used herein are provided for convenience only and have their conventional meanings and denote those portions of the inhibitor believed to fill the S1, S2 and S3 subsites respectively of the enzyme, where S1 is adjacent the cleavage site and S3 remote from the cleavage site.

A further aspect of the invention comprises a method employing the compounds of formula I for the prophylaxis or treatment of diseases caused by aberrant expression or activation of cathepsin, i.e. diseases or conditions alleviated or modified by inhibition of cathepsin S, preferably without substantial concomitant inhibition of other members of the papain superfamily.

In a preferred aspect, the invention concerns a method employing the compounds of formula I or any subgroup thereof as specified herein, for the treatment of diseases caused by aberrant expression or activation of cathepsin, i.e. diseases or conditions alleviated or modified by inhibition of cathepsin S, preferably without substantial concomitant inhibition of other members of the papain superfamily.

A further aspect of the invention provides the use of the compounds of formula I prophylaxis or treatment of diseases caused by aberrant expression or activation of cathepsin, ie diseases or conditions alleviated or modified by inhibition of cathepsin S, preferably without substantial concomitant inhibition of other members of the papain superfamily.

In a preferred aspect, the invention concerns the use of compounds of formula I or any subgroup thereof as specified herein, for the treatment of diseases caused by aberrant expression or activation of cathepsin, i.e. diseases or conditions alleviated or modified by inhibition of cathepsin S, preferably without substantial concomitant inhibition of other members of the papain superfamily A further aspect of the invention provides the use of the compounds of formula I for the manufacture of a medicament for the prophylaxis or treatment of diseases caused by aberrant expression or activation of cathepsin S, i.e. diseases or conditions alleviated or modified by inhibition of cathepsin S, preferably without substantial concomitant inhibition of other members of the papain superfamily.

In a preferred aspect, the invention concerns the use of compounds of formula I or any subgroup thereof as specified herein, for the manufacture of a medicament for the treatment of diseases caused by aberrant expression or activation of cathepsin S, i.e. diseases or conditions alleviated or modified by inhibition of cathepsin S, preferably without substantial concomitant inhibition of other members of the papain superfamily.

Examples of such diseases or conditions defined in the immediately preceding three paragraphs include those enumerated in WO 97/40066, such as autoimmune diseases, allergies, such as asthma and hay fever, multiple sclerosis, rheumatoid arthritis and the like. A further example is the treatment of endometriasis, and especially chronic pain, as disclosed in WO03/20287. The invention further provides the use of the compounds of formula I or any subgroup of formula I in therapy and in the manufacture of a medicament for the treatment of diseases or conditions alleviated or moderated by inhibition of cathepsin S.

In one series of embodiments, the methods are employed to treat mammals, particularly humans at risk of, or afflicted with, autoimmune disease. By autoimmunity is meant the phenomenon in which the host's immune response is turned against its own constituent parts, resulting in pathology. Many human autoimmune diseases are associated with certain class II MHC-complexes. This association occurs because the structures recognized by T cells, the cells that cause autoimmunity, are complexes comprised of class II MHC molecules and antigenic peptides. Autoimmune disease can result when T cells react with the host's class II MHC molecules when complexed with peptides derived from the host's own gene products. If these class II MHC/antigenic peptide complexes are inhibited from being formed, the autoimmune response is reduced or suppressed. Any autoimmune disease in which class II MHC/antigenic complexes play a role may be treated according to the methods of the present invention.

Such autoimmune diseases include, e.g., juvenile onset diabetes (insulin dependent), multiple sclerosis, pemphigus vulgaris, Graves' disease, myasthenia gravis, systemic lupus erythematosus, rheumatoid arthritis and Hashimoto's thyroiditis.

In another series of embodiments, the methods are employed to treat mammals, particularly humans, at risk of, or afflicted with, allergic responses. By "allergic response" is meant the phenomenon in which the host's immune response to a particular antigen is unnecessary or disproportionate, resulting in pathology. Allergies are well known in the art, and the term "allergic response" is used herein in accordance with standard usage in the medical field.

Examples of allergies include, but are not limited to, allergies to pollen, "ragweed," shellfish, domestic animals (e.g., cats and dogs), bee venom, house dust mite allergens and the like. Another particularly contemplated allergic response is that which causes asthma. Allergic responses may occur, in man, because T cells recognize particular class II MHC/antigenic peptide complexes. If these class II MHC/antigenic peptide complexes are inhibited from being formed, the allergic response is reduced or suppressed. Any allergic response in which class II MHC/antigenic peptide complexes play a role may be treated according to the methods of the present invention. Immunosuppression by the methods of the present invention will typically be a prophylactic or therapeutic treatment for severe or life-threatening allergic responses, as may arise during asthmatic attacks or anaphylactic shock. Preferably, the treatment is a therapeutic treatment.

In another series of embodiments, the methods are employed to treat mammals, particularly humans, which have undergone, or are about to undergo, an organ transplant or tissue graft. In tissue transplantation (e.g., kidney, lung, liver, heart) or skin grafting, when there is a mismatch between the class II MHC genotypes (HLA types) of the donor and recipient, there may be a severe "allogeneic" immune response against the donor tissues which results from the presence of non-self or allogeneic class II MHC molecules presenting antigenic peptides on the surface of donor cells. To the extent that this response is dependent upon the formation of class II MHC/antigenic peptide complexes, inhibition of cathepsin S may suppress this response and mitigate the tissue rejection. An inhibitor of cathepsin S can be used alone or in conjunction with other therapeutic agents, e.g., as an adjunct to cyclosporin A and/or antilymphocyte gamma globulin, to achieve immunosuppression and promote graft survival. Preferably, administration is accomplished by systemic application to the host before and/or after surgery. Alternatively or in addition, perfusion of the donor organ or tissue, either prior or subsequent to transplantation or grafting, may be effective.

The above embodiments have been illustrated with an MHC class II mechanism but the invention is not limited to this mechanism of action. Suppression of cathepsin S as a treatment of COPD or chronic pain may not, for example, involve MHC class II at all.

A related aspect of the invention is directed to a method of treating a patient undergoing a therapy wherein the therapy causes an immune response, preferably a deleterious immune response, in the patient comprising administering to the patient a compound of Formula I or a pharmaceutically acceptable salt, n-oxide or hydrate thereof. Typically, the immune response is mediated by MHC class II molecules. The compound of this invention can be administered prior to, simultaneously, or after the therapy. Typically, the therapy involves treatment with a biologic, such as a protein, preferably an antibody, more preferably a monoclonal antibody. More preferably, the biologic is Remicade®, Refacto®, ReferonA®, Factor VIII, Factor VII, Betaseron®, Epogen®, Enbrel®, Interferon beta, Botox®, Fabrazyme®, Elspar®, Cerezyme®, Myobloc®, Aldurazyme®, Verluma®, Interferon alpha, Humira®, Aranesp®, Zevalin® or OKT3. Alternatively the treatment involves use of heparin, low molecular weight heparin, procainamide or hydralazine.

Assays for the assessment of cathepsin S inhibitors in the treatment of chronic pain, including neuropathic or inflammatory pain are as described in WO 03/20287.

Currently preferred indications treatable in accordance with the present invention include:

Psoriasis;

Autoimmune indications, including idiopathic thrombocytopenic purpura (ITP), rheumatoid arthritis (RA), multiple schlerosis (MS), myasthenia gravis (MG), Sjögrens syndrome, Grave's disease and systemic lupus erythematosis (SLE);

Non-automimmune indications include allergic rhinitis, asthma, artherosclerosis, chronic obstructive pulmonary disease (COPD) and chronic pain.

The compounds of the invention can form salts which form an additional aspect of the invention. Appropriate pharmaceutically acceptable salts of the compounds of the invention include salts of organic acids, especially carboxylic acids, including but not limited to acetate, trifluoroacetate, lactate, gluconate, citrate, tartrate, maleate, malate, pantothenate, isethionate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, propionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids.

The compounds of the invention may in some cases be isolated as the hydrate. Hydrates are typically prepared by recrystallisation from an aqueous/organic solvent mixture using organic solvents such as dioxin, tetrahydrofuran or methanol. Hydrates can also be generated in situ by administration of the corresponding keton to a patient.

The N-oxides of compounds of the invention can be prepared by methods known to those of ordinary skill in the art. For example, N-oxides can be prepared by treating an unoxidized form of the compound of the invention with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds of the invention can be prepared from the N-oxide of an appropriate starting material.

Compounds of the invention in unoxidized form can be prepared from N-oxides of the corresponding compounds of the invention by treating with a reducing agent (e.g., sulphur, sulphur dioxide, triphenyl phosphine, lithium borohydride, sodium borohydride, phosphorus dichloride, tribromide, or the like) in an suitable inert organic solvent (e.g., acetonitrile, ethanol, aqueous dioxane, or the like) at 0 to 80° C.

The present invention also includes isotope-labelled compounds of formula I or any subgroup of formula I, wherein one or more of the atoms is replaced by an isotope of that atom, i.e. an atom having the same atomic number as, but an atomic mass different from, the one(s) typically found in nature. Examples of isotopes that may be incorporated into the compounds of formula I or any subgroup of formula I, include but are not limited to isotopes of hydrogen, such as $^2$H and $^3$H (also denoted D for deuterium and T for tritium respectively), carbon, such as $^{11}$C, $^{13}$C and $^{14}$C, nitrogen, such as $^{13}$N and $^{15}$N, oxygen, such as $^{15}$O, $^{17}$O and $^{18}$O, phosphorus, such as $^{31}$P and $^{32}$P, sulphur, such as $^{35}$S, fluorine, such as $^{18}$F, chlorine, such as $^{36}$Cl, bromine such as $^{75}$Br, $^{76}$Br, $^{77}$Br and $^{82}$Br, and iodine, such as $^{123}$I, $^{124}$I, $^{125}$I and $^{131}$I.

The choice of isotope included in an isotope-labelled compound will depend on the specific application of that compound. For example, for drug or substrate tissue distribution assays, compounds wherein a radioactive isotope such as $^3$H or $^{14}$C is incorporated will generally be most useful. For radio-imaging applications, for example positron emission tomography (PET) a positron emitting isotope such as $^{11}$C, $^{18}$F, $^{13}$N, or $^1$O will be useful. The incorporation of a heavier isotope, such as deuterium, i.e. $^2$H, may provide greater metabolic stability to a compound of formula I or any subgroup of formula I, which may result in, for example, an increased in vivo half life of the compound or reduced dosage requirements. For example, $^2$H isotope(s) are typically incorporated at position(s) disposed to metabolic liability. In the compounds of the present invention, suitable positions for incorporation of $^2$H isotopes are e.g. as substituents to the 1,1-cycloalkylene group, i.e. one or both of $R^{2a}$ and $R^{2b}$ is $^2$H.

Isotopically labelled compounds of formula I or any subgroup of formula I can be prepared by processes analogous to those described in the Schemes and/or Examples herein below by using the appropriate isotopically labelled reagent or starting material instead of the corresponding non-isotopically labelled reagent or starting material, or by conventional techniques known to those skilled in the art.

It should be noted that the radical positions on any molecular moiety used in the definitions may be anywhere on such moiety as long as it is chemically stable.

As used herein, the following terms have the meanings as defined below:

$C_m$-$C_n$alkyl used on its own or in composite expressions such as $C_m$-$C_n$haloalkyl, $C_m$-$C_n$alkylcarbonyl, $C_m$-$C_n$alkylamine, $C_m$-$C_n$alkylsulphonyl, $C_m$-$C_n$alkylsulfonylamino etc. represents a straight or branched alkyl radical having the number of carbon atoms designated, e.g. $C_1$-$C_4$alkyl means an alkyl radical having from 1 to 4 carbon atoms. Preferred alkyl radicals for use in the present invention are $C_1$-$C_4$alkyl and includes methyl, ethyl, n-propyl, isopropyl, t-butyl, n-butyl and isobutyl. Methyl and t-butyl are typically preferred. $C_1$-$C_6$alkyl has a corresponding meaning, including also all straight and branched chain isomers of pentyl and hexyl. Other recitals of $C_m$-$C_n$alkyl, such as $C_5$-$C_{10}$ alkyl have the corresponding meaning.

The term Me means methyl, MeO means methoxy, Et means ethyl and Ac means acetyl.

$C_0$-$C_2$alkylene used in composite expressions such as $C_3$-$C_6$cycloalkyl$C_0$-$C_2$alkylene refers to a divalent radical derived from a methyl or ethyl group, or in the case of $C_0$ the term $C_0$-$C_2$alkylene means a bond.

$C_1$-$C_4$haloalkyl refers to $C_1$-$C_4$alkyl, wherein at least one C atom is substituted with a halogen, preferably chloro or fluoro. Trifluoromethyl is typically preferred $C_1$-$C_4$alkoxy represents a radical $C_1$-$C_4$alkyl-O wherein $C_1$-$C_4$alkyl is as defined above, and includes methoxy, ethoxy, n-propoxy, isopropoxy, t-butoxy, n-butoxy and isobutoxy. Methoxy and isopropoxy are typically preferred. $C_1$-$C_6$alkoxy has a corresponding meaning, expanded to include all straight and branched chain isomers of pentoxy and hexoxy. Other recitals of $C_m$-$C_n$alkoxy, such as $C_5$-$C_{10}$alkoxy have the corresponding meaning.

$C_1$-$C_4$haloalkoxy as used herein is meant to include $C_1$-$C_4$alkoxy wherein at least one C-atom is substituted with one or more halogen atom(s), typically chloro or fluoro. In many cases trifluoromethyl is preferred.

$C_1$-$C_4$alkoxycarbonyl means a radical $C_1$-$C_4$alkyl-O—C(=O).

Carbocyclyl includes cyclopentyl, cyclohexyl and especially cyclopropyl and cyclobutyl. Carbocyclyl further includes cyclopentenyl and cyclohexenyl, in each case with a single double bond. A frequently preferred value for Carbocyclyl is phenyl.

Cyclic amine includes aziridine, azetidine, pyrrolidine, piperidine, piperazine and morpholine.

Het is a stable, monocyclic or bicyclic, saturated, partially saturated or aromatic ring system, containing 1-4 hetero atoms independently selected from O, S and N, and each ring having 5 or 6 ring atoms; Exemplary aromatic Het include furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole and the like. Exemplary unsaturated Het include tetrahydrofuran, pyran, dihydropyran, 1,4-dioxane, 1,3-dioxane, piperidine, pyrrolidine, morpholine, tetrahydrothiopyran, tetrahydrothiophene, 2-H-pyrrole, pyrroline, pyrazoline, imidazoline, thiazolidine, isoxazolidine and the like.

The compounds of the invention include a number of handles such as OH, NH or COOH groups to which conventional prodrug moieties can be applied. Prodrugs are typically hydrolysed in vivo to release the parent compound in the plasma, liver or intestinal wall. Favoured prodrugs are esters of hydroxyl groups such as a phenolic hydroxyl group at $R^4$, or amine functions such as a sulphonamide amine function. Preferred pharmaceutically acceptable esters include those derived from $C_1$-$C_6$ carboxylic acids such as acetyl or pivaloyl or optionally substituted benzoic acid esters, preferably unsubstituted or substituted with substituents broadly as described for $R^{1a}$, typically 1-3 halo (e.g. F), $C_1$-$C_4$alkyl (e.g. Me), $C_1$-$C_4$haloalkyl (e.g. $CF_3$) or $C_1$-$C_4$alkyloxy (e.g. MeO) groups. Favoured sulphonamide prodrugs include aminoacyls derived from $C_1$-$C_6$ carboxylic acids such as acetyl or pivaloyl or optionally substituted benzoic acid esters, preferably unsubstituted or substituted with substituents broadly as described for variable $R^{1a}$, typically 1-3 halo (e.g. F), $C_1$-$C_4$alkyl (e.g. Me), $C_1$-$C_4$haloalkyl (e.g. $CF_3$) or $C_1$-$C_4$alkyloxy (e.g. MeO) groups.

Unless otherwise mentioned or indicated, the chemical designation of a compound encompasses the mixture of all possible stereochemically isomeric forms, which said compound may possess. Said mixture may contain all diastereomers and/or enantiomers of the basic molecular structure of said compound. All stereochemically isomeric forms of the compounds of the present invention both in pure form or mixed with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i e minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Compounds of the invention can be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diasteromeric derivatives of compounds of Formula I, dissociable complexes are preferred (e.g., crystalline; diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography, for example HPLC or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

While it is possible for the active agent to be administered alone, it is preferable to present it as part of a pharmaceutical formulation. Such a formulation will comprise the above defined active agent together with one or more acceptable carriers/excipients and optionally other therapeutic ingredients. The carrier(s) must be acceptable in the sense of being compatible with the other ingredients of the formulation and not deleterious to the recipient.

The formulations include those suitable for rectal, nasal, topical (including buccal and sublingual), vaginal or parenteral (including subcutaneous, intramuscular, intravenous and intradermal) administration, but preferably the formulation is an orally administered formulation. The formulations may conveniently be presented in unit dosage form, e.g. tablets and sustained release capsules, and may be prepared by any methods well known in the art of pharmacy. Such methods include the step of bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of Formula I or its pharmaceutically acceptable salt in conjunction or association with a pharmaceutically acceptable carrier or vehicle. If the manufacture of pharmaceutical formulations involves intimate mixing of pharmaceutical excipients and the active ingredient in salt form, then it is often preferred to use excipients which are non-basic in nature, i.e. either acidic or neutral.

Formulations for oral administration in the present invention may be presented as discrete units such as capsules, cachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion and as a bolus etc.

With regard to compositions for oral administration (e.g. tablets and capsules), the term suitable carrier includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring or the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatine and glycerine, or sucrose and acacia; and mouthwashes comprising the active agent in a suitable liquid carrier.

As with all pharmaceuticals, the appropriate dosage for the compounds or formulations of the invention will depend upon the indication, the severity of the disease, the size and metabolic vigour and the patient, the mode of administration and is readily determined by conventional animal trials. Dosages providing intracellular (for inhibition of physiological proteases of the papain superfamily) concentrations of the order 0.01-100 µM, more preferably 0.01-10 µM, such as 0.1-5 µM are typically desirable and achievable.

Compounds of the invention are prepared by a variety of solution and solid phase chemistries.

A typical first step is the preparation of a P1 building block of the formula III

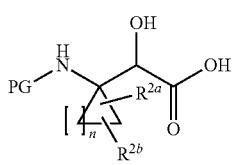

(III)

where $R^{2a}$ and $R^{2b}$ are as defined above and PG is a conventional N protecting group such as Boc, CBz or Fmoc. These building blocks are novel and constitute a further aspect of the invention. The P1 building block (III) is subsequently transformed into a P1-prime side unit of formula (IV)

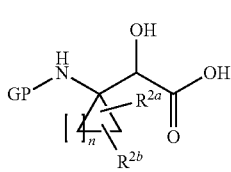

(IV)

where $R^{2a}$ and $R^{2b}$ are as defined above and PG is a conventional N protecting group such as Boc, CBz or Fmoc. These building blocks are novel and constitute a further aspect of the invention.

Building blocks of formula III and IV are typically prepared as described in scheme 1 below.

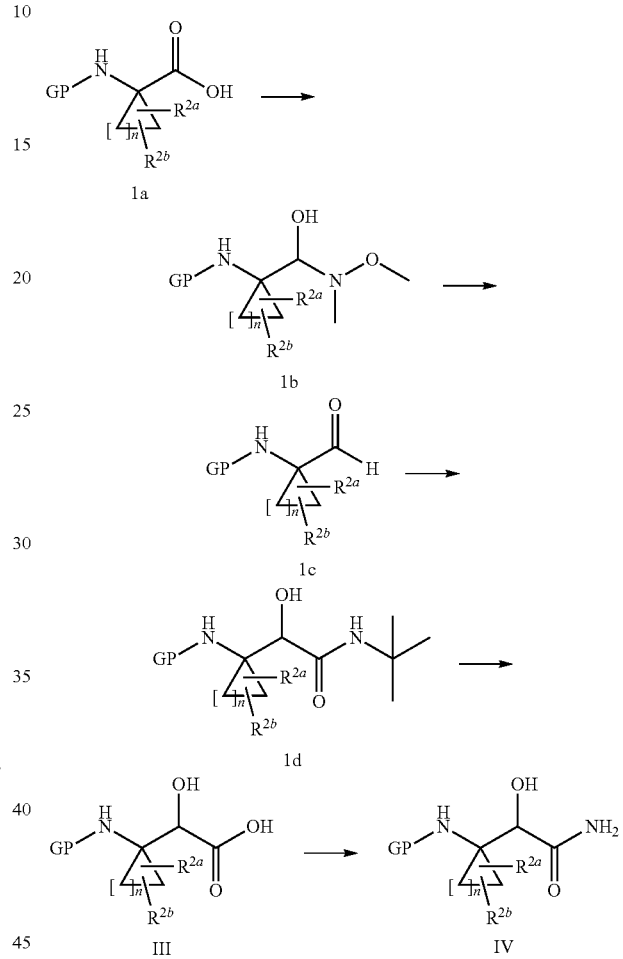

A suitable starting material is an N-protected cycloalkyl amino acid, of which several are available commercially or can be prepared as shown in the following Examples or as described by Allan et al. in J. Med. Chem., 1990 33(10) 2905-2915.

The carboxylic acid (1a) is transformed via a Weinreb synthesis to a N,O-dimethylhydroxamic acid (1b) which provides the corresponding aldehyde (1c). The aldehyde may also be accessed by reduction of the carboxylic function of a cycloalkyl amino acid followed by oxidation under Dess Martin conditions. The aldehyde (1c) can be subsequently reacted with t.butyl isocyanide or equivalent in a Passerini reaction to afford the α-hydroxy amide (1d). Subsequent hydrolysis of the amide then provides the required α-hydroxycarboxylic acid P1 building block (III). Generally the strongly acidic conditions required to hydrolyse the amide also lead to loss of the NBoc protection, if used. Hence, the amine can be used directly to couple to a P2 building block or else if it needs to be stored, the amine can be reprotected. The P1 building block (III) is then modified at the C terminus to provide the primary amide P1-prime side unit (IV). Typically the P1 building block (III) is transformed to a primary amide via the methyl ester by reaction with methyl iodide in the presence of a suitable base, such as potassium carbonate or the like, followed by hydrolysis of the intermediate methyl ester to the primary amide effected for instance by treatment with a saturated solution of ammonia in methanol.

P1-prime side unit IV thus afforded is then extended at N terminus to provide compounds of formula I. Scheme 2 below illustrates a route to compounds of formula I wherein $R^4$ is $C_1$-$C_6$alkyl, $C_1$-$C_6$haloalkyl, Het or Carbocyclyl.

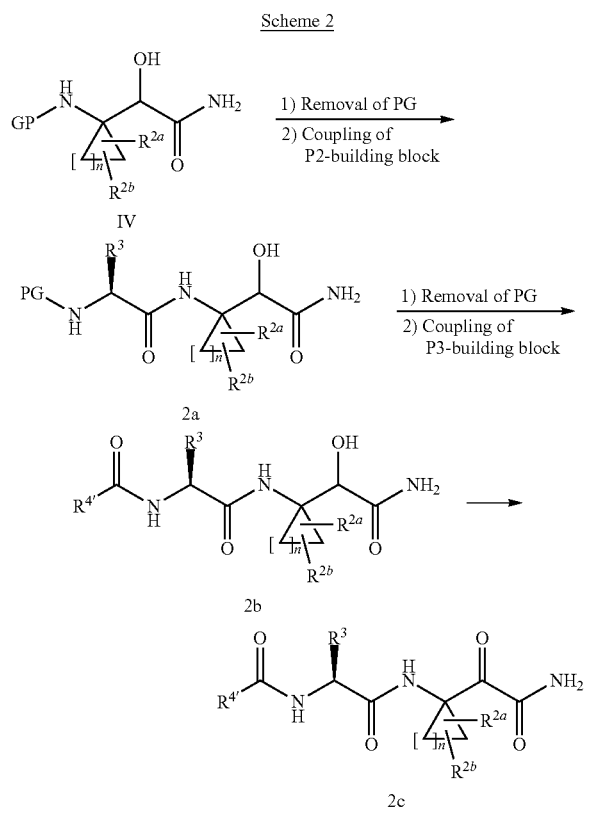

$R^{4'}$ is $C_1$-$C_6$alkyl, $C_1C_6$haloalkyl, Het or Carbocyclyl

The P1-prime side unit (IV) is deprotected at the N terminus and elongated with the P2 and subsequently P3 building blocks using conventional peptide chemistries. For example a P2 residue can be introduced via BocP2-OH using standard coupling conditions such as HATU, DIPEA in DMF. The terminal Boc protection is again removed with acetyl chloride in methanol or equivalent and the P3 residue introduced via P3-OH using standard coupling conditions such as HATU, DIPEA in DMF. Alternatively, A P3-P2-building block may be prepared separately and added directly to the P1-prime side-building block (IV) in one step, thus affording the dipeptide derivative (2b). Oxidation of the α-hydroxy amide to the corresponding α-keto amide (2c) is then effected using any convenient oxidation method known in the art, such as Dess Martin oxidation or Moffat oxidation or the like.

Compounds of formula II, i.e. compounds wherein $R^4$ is $C_1$-$C_6$alkoxy, $C_1$-$C_6$haloalkoxy, can be prepared from the N-protected amine 2a as generally illustrated in scheme 3.

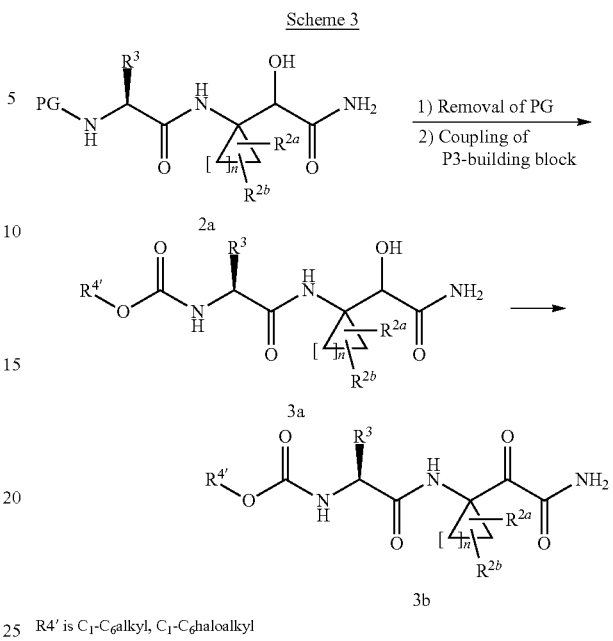

$R^{4'}$ is $C_1$-$C_6$alkyl, $C_1$-$C_6$haloalkyl

Removal of the N-protecting group from the N-protected amine (2a) using standard techniques well known in the art of peptide synthesis, such as treatment with acid in the case of a boc-protecting group, followed by reaction with a suitable alkoxycarbonylating agent such as an alkyl chloroformate or a dialkyl dicarbonate, optionally in the presence of a base such as diisopropylethyl amine or similar, provides the carbamate (3a). Oxidation of the α-hydroxy amide to the corresponding α-keto amide (3b) is then effected using any convenient oxidation method known in the art, such as Dess Martin oxidation or Moffat oxidation or the like.

An extensive range of appropriately protected L-amino acids suitable for P2 building blocks and carboxylic acids, carboxylic acid halides and carbamoyl halides suitable for P3 building blocks are commercially available or accessed by simple chemistries or as shown in WO06/064286. The P3 and P2 building blocks may alternatively be coupled first and then reacted with the P1-prime side unit.

Elongation is typically carried out in the presence of a suitable coupling agent e.g., benzotriazole-1-yloxytrispyrrolidinophosphonium hexafluorophosphate (PyBOP), O-benzotriazol-1-yl-N,N,N',N'-tetramethyl-uronium hexafluorophosphate (HBTU), O-(7-azabenzotriazol-1-yl-1,1,3,3-tetramethyl-uronium hexafluorophosphate (HATU), 1-(3-dimethylaminopropyl)-3-ethylcarbodiimide hydrochloride (EDC), or 1,3-dicyclohexyl carbodiimide (DCC), optionally in the presence of 1-hydroxybenzotriazole (HOBT), and a base such as N,N-diisopropylethylamine, triethylamine, N-methylmorpholine, and the like. The reaction is typically carried out at 20 to 30° C., preferably at about 25° C., and requires 2 to 24 h to complete. Suitable reaction solvents are inert organic solvents such as halogenated organic solvents (e.g., methylene chloride, chloroform, and the like), acetonitrile, N,N-dimethylformamide, ethereal solvents such as tetrahydrofuran, dioxane, and the like.

Alternatively, the above elongation coupling step can be carried out by first converting the P3/P2 building block into an active acid derivative such as succinimide ester and then reacting it with the P1 amine. The reaction typically requires 2 to 3 h to complete. The conditions utilized in this reaction depend on the nature of the active acid derivative. For example, if it is an acid chloride derivative, the reaction is carried out in the presence of a suitable base (e.g. triethylamine, diisopropylethylamine, pyridine, and the like). Suitable reaction solvents are polar organic solvents such as acetonitrile, N,N-dimethylformamide, dichloromethane, or any suitable mixtures thereof.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in Greene, "Protective Groups in Organic Synthesis" (John Wiley & Sons, New York, 1981), which is hereby incorporated by reference. N-protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl, and the like, carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butoxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl, and the like; alkyl groups such as benzyl, triphenylmethyl, benzyloxymethyl and the like; and silyl groups such as trimethylsilyl and the like. Favoured N-protecting groups include formyl, acetyl, benzoyl, pivaloyl, t-butylacetyl, phenylsulfonyl, benzyl (bz), t-butoxycarbonyl (BOC) and benzyloxycarbonyl (Cbz).

Hydroxy and/or carboxy protecting groups are also extensively reviewed in Greene ibid and include ethers such as methyl, substituted methyl ethers such as methoxymethyl, methylthiomethyl, benzyloxymethyl, t-butoxymethyl, 2-methoxyethoxymethyl and the like, silyl ethers such as trimethylsilyl (TMS), t-butyldimethylsilyl (TBDMS) tribenzylsilyl, triphenylsilyl, t-butyldiphenylsilyl triisopropyl silyl and the like, substituted ethyl ethers such as 1-ethoxymethyl, 1-methyl-1-methoxyethyl, t-butyl, allyl, benzyl, p-methoxybenzyl, dipehenylmethyl, triphenylmethyl and the like, aralkyl groups such as trityl, and pixyl (9-hydroxy-9-phenylxanthene derivatives, especially the chloride). Ester hydroxy protecting groups include esters such as formate, benzylformate, chloroacetate, methoxyacetate, phenoxyacetate, pivaloate, adamantoate, mesitoate, benzoate and the like. Carbonate hydroxy protecting groups include methyl vinyl, allyl, cinnamyl, benzyl and the like.

DETAILED DESCRIPTION OF THE EMBODIMENTS

Various embodiments of the invention will now be described by way of illustration only with reference to the following Examples.

In the examples below, the following systems are typically employed:

Nuclear Magnetic Resonance (NMR) spectra were recorded on a Varian Gemini 7 Tesla 300 MHz instrument, or a Bruker Avance 400 MHz instrument in the solvent indicated. Chemical shifts are given in ppm down- and upfield from tetramethylsilane (TMS). Resonance multiplicities are denoted s, d, t, m, br and app for singlet, doublet, triplet, multiplet, broad and apparent, respectively. The Mass Spectrometry (MS) spectra were recorded on a Finnigan SSQ7000 TSP or a Finnigan SSQ710 DI/EI instrument. LC-MS was obtained with a Waters 2790 LC-system equipped with a Waters Xterra™ MS $C_8$ 2.5 μm 2.1×30 mm column, a Waters 996 Photodiode Array Detector and a Micromass ZMD. High pressure liquid chromatography (HPLC) assays were performed using a Hewlett Packard 1100 Series HPLC system equipped with a Zorbax column SB-$C_8$ 4.6 mm×15 cm. Column chromatography was performed using silica gel 60 (230-400 mesh ASTM, Merck) and thin layer chromatography (TLC) was performed on TLC precoated plates, silica gel 60 $F_{254}$ (Merck).

Preparation of Building Block 1 (BB1), a P1 Building Block

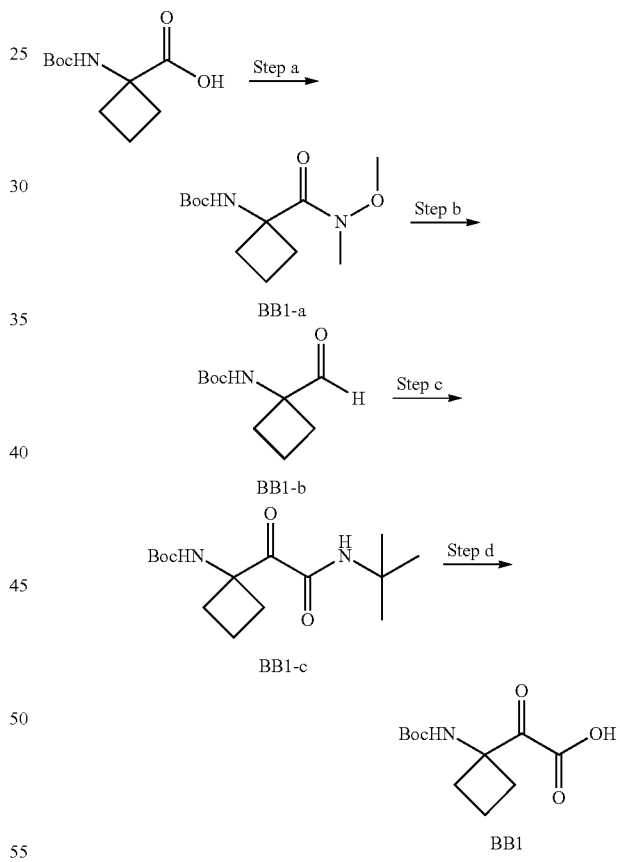

Step a) 2-(1-((tert-butoxycarbonyl)amino)cyclobutyl)-2-hydroxyacetic acid (BB1-a)

To a solution of 1-tert-butoxycarbonylamino-cyclobutanecarboxylic acid (3 g, 13.94 mmol) in dry DMF (50 mL) was added N,O-dimethylhydroxylamine×HCl (1.36 g, 13.94 mmol) and DIEA (9.21 mL, 55.75 mmol). The reaction flask was cooled to 0° C. and after 10 minutes HATU (5.30 g, 13.94 mmol) was added to the solution (which turned yellow on addition). After 2 hrs the DMF was removed by rotary evaporation at reduced pressure. The residue was dissolved in EtOAc (100 mL) and washed twice with 10% citric acid (aq) and saturated NaHCO₃(aq) solution. The organic phase was dried with Na₂SO₄, filtered and evaporated on silica. The product was purified by flash chromatography (heptane: ethyl acetate (1:1) to give the product as a colourless oil that slowly crystallizes (3.13 g) in 87% yield.

Step b) (1-Formyl-cyclobutyl)-carbamic acid tert-butyl ester (BB1-b)

LiAlH₄ (202 mg, 5.33 mmol) was added to a solution of the Weinreb amide BB1-a (1.10 g, 4.27 mmol) dissolved in dry diethyl ether (35 mL) at 0° C. The solution was stirred at 15 minutes before the reaction was quenched with slow addition of potassium hydrogen tartaric acid (sat, aq) and stirred for 10 minutes. The solution was poured into a separatory funnel and the water phase was extracted with ethyl acetate twice. The combined organic phases were washed with 0.5 M HCl (3 times), NaHCO₃(aq) (2 times) and brine (1 time). The organic phase was dried with Na₂SO₄, filtered and evaporated on silica. The product was purified by flash chromatography (heptane: ethyl acetate (4:1→3:1) to give the product as white crystals (0.647 g) in 76% yield.

Step c) [1-(tert-Butylcarbamoyl-hydroxy-methyl)-cyclobutyl]-carbamic acid tert-butyl ester (BB 1-c)

BB1-b, (1.75 g, 8.78 mmol) was dissolved in CH₂Cl₂ (18 mL) and cooled in an ice bath, under inert gas. Pyridine (2.85 mL) was added, followed by t-butyl isocyanide (1.50 mL, 13.3 mmol). Trifluoroacetic acid (1.35 mL, 17.5 mmol) was then added dropwise over 30 min. The yellow solution was stirred at RT overnight. The mixture was concentrated, diluted with EtOAc (100 mL) and washed successively with 1N HCl (50 mL), saturated NaHCO₃ (50 mL) and saturated NaCl (2×50 mL). Drying (Na₂SO₄) and concentration under vacuum. The afforded crude product was treated with THF (2.5 mL) and 1M LiOH in 3/1 MeOH-water (2.5 mL) at RT. TLC (3/1 petroleum ether—EtOAc) showed complete ester hydrolysis after 15 min. After 45 min reaction time, 1N HCl (2.5 mL), water (10 mL) and EtOAc (20 mL) were added, and the layers were separated. The organic phase was washed with saturated NaHCO₃ (20 mL) and then saturated NaCl (2×20 mL), dried (Na₂SO₄) and concentrated. Flash chromatography (75 g silica, 5/1 to 1/1 petroleum ether—EtOAc) gave a white solid (2.36 g, 89%).

Step d (1-tert-Butoxycarbonylamino-cyclobutyl)-hydroxy-acetic acid (BB1)

BB1-c (1.30 g, 4.33 mmol) was refluxed with 6N HCl (40 mL) until amide hydrolysis was complete as monitored by LCMS. The mixture was evaporated, co-evaporating several times with water. 1M NaOH (15 mL) was added to the residue and the basic solution was stirred under vacuum for 15 min Boc₂O (1.92 g, 8.80 mmol) in dioxane (10 mL) was added, keeping pH at 10-11, and the mixture was stirred at RT overnight. The mixture was diluted with water (50 mL), acidified with 1N HCl to pH 3, in an ice bath, and then extracted with EtOAc (2×50 mL, then 30 mL). The organic phase was washed with saturated NaCl (50 mL), dried (Na₂SO₄) and evaporated to give crude P1 building block BB1 (0.649 g).

$^{1H}$NMR (400 MHz, d₆-DMSO) δ 6.88 (br s, 1H), 4.15 (s, 1H), 2.40 (br m, 2H), 1.98 (br m, 2H), 1.80 (br m, 2H), 1.35 (s, 9H); ms ES⁺ m/z 146 (100%), 190 (50%).

Preparation of Building Block 2 (BB2), a P1 Building Block

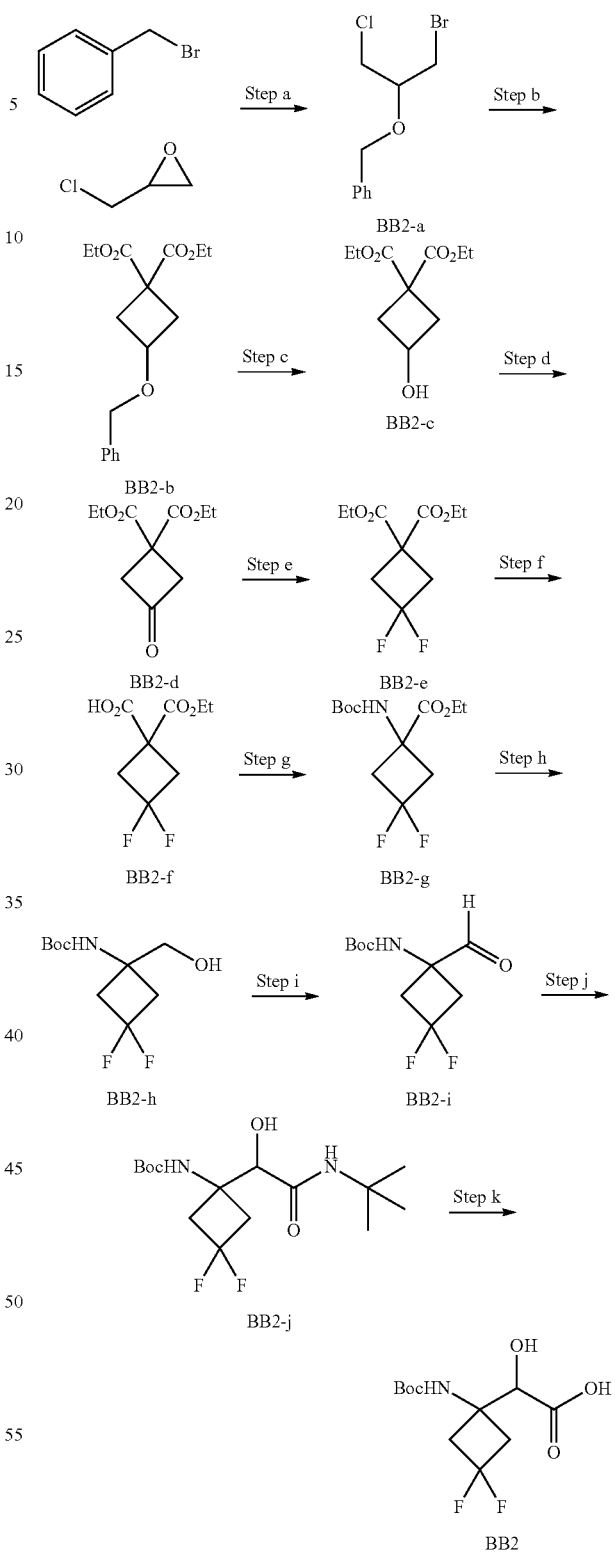

Step a) ((1-Bromo-3-chloropropan-2-yloxy)methyl)benzene (BB2-a)

To a stirred mixture of benzyl bromide (185 g, 1.08 mol) and (1.5 g) of mercurous chloride was added epichlorohydrin (100 g, 1.08 mol). The reaction mixture was heated for 12 hr at 100° C. TLC analysis confirmed formation of product. The product was separated from the dark brown reaction mixture by column chromatography using petroleum ether as eluent. TLC system; Petroleum ether: ethyl acetate (9:1), $R_F$=0.7. Yield; 148 g, 51%.

Step b) 3-Benzyloxy-cyclobutane-1,1-dicarboxylic acid diethyl ester (BB2-b)

To a stirred suspension of sodium hydride (22.5 g, 0.562 mol) in 800 mL of dry dioxane, was added diethyl malonate (90 g, 0.562 mol) drop-wise over 20 min After this addition was complete, BB2-a (148 g, 0.56 mol) was added drop-wise over 20 min The mixture was then heated at reflux for 24 hr. After cooling to room temperature, sodium hydride (22.5 g, 0.562 mol) in a little dioxane (~20 mL) was added to the mixture and heating at reflux was continued for an additional 48 hr. The solvent was partially removed under reduced pressure and the mixture was treated with 800 mL of water. This mixture was then extracted with ethyl acetate (500 mL×3), extracts were dried ($Na_2SO_4$) and concentrated in vacuo and the residue was purified by column chromatography using petroleum ether: ethyl acetate (10%) which gave the title compound. TLC system; petroleum ether: ethyl acetate (9:1), $R_F$=0.3. Yield: 100 g, 58%

Step c) Diethyl 3-hydroxycyclobutane-1,1-dicarboxylate (BB2-c)

To a solution of compound BB2-b (40 g) in EtOH (500 mL) was added 10% palladium on charcoal (4 g) and the mixture was hydrogenated for 3.5 hours at 50 psi at room temperature. The catalyst was removed by filtration, washed with ethyl acetate, EtOH and the solvent was then removed under reduced pressure. The residue was purified by silica gel chromatography with hexane/ethyl acetate as eluent to provide the title compound. TLC system; Petroleum ether: ethyl acetate (9:1), $R_F$=0.3. Yield: 18 g, 64%.

Step d) Diethyl 3-oxocyclobutane-1,1-dicarboxylate (BB2-d)

To a solution of compound BB2-c (18 g, 0.0833 mol) in DCM (200 mL) was added PCC (37 g, 0.176 mol) and the mixture was stirred for four hours at room temperature. The solution was filtered through a silica gel column and the residue was washed with DCM/MeOH 98/2 and then filtered through a similar column. The combined fractions were evaporated under reduced pressure to provide the desired compound. TLC system; Petroleum ether: ethyl acetate (9:1), $R_F$=0.3. Yield: 11 g, 62%.

Step e) Diethyl 3,3-difluorocyclobutane-1,1-dicarboxylate (BB2-e)

To a cooled solution of compound BB2-d (11 g, 0.0513 mol) in dry DCM (150 mL) was added drop-wise a solution of DAST (18.72 g, 0.116 mol) and the mixture was stirred at room temperature overnight. The mixture was added to ice water and was extracted three times with DCM. The solution was dried with sodium sulphate and evaporated under reduced pressure. The residue was purified by silica gel chromatography employing hexane/ethyl acetate as eluent to provide the title compound. TLC system; Petroleum ether: ethyl acetate (7:3), $R_F$=0.5. Yield: 7.7 g, 64%.

Step f) 1-(Ethoxycarbonyl)-3,3-difluorocyclobutan-ecarboxylic acid (BB2-f)

Compound BB2-e (7.7 g, 0.0325 mol) was dissolved in ice cooled 0.5 M ethanolic potassium hydroxide solution (30 mL) and water (6 mL). The mixture was stirred at room temperature overnight. Water was added and most of the ethanol was removed under reduced pressure. The mixture was acidified with 2M HCl and extracted three times with ethyl acetate. The organic phase was dried with sodium sulphate and evaporated under reduced pressure to give the desired compound. TLC system: petroleum ether: ethyl acetate (1:1), $R_F$=0.3. Yield: 5.8 g, 86%.

Step g) Ethyl 1-(tert-butoxycarbonylamino)-3,3-difluorocyclobutanecarboxylate (BB2-g)

To a solution of compound BB2-f (5.8 g, 0.0273 mol) in dry dioxane (100 mL) was added tert-butanol (24.4 mL), DPPA (7.87 g, 0.027 mol) and TEA (2.87 g, 0.0284 mol) and the mixture was refluxed for five hours. Ethyl acetate (about 200 mL) was added and the organic phase was washed twice with 5% citric acid and saturated sodium hydrogen carbonate. The solution was dried and evaporated under reduced pressure. The desired product was isolated by silica gel chromatography with hexane/ethyl acetate. TLC system; Petroleum ether: ethyl acetate (1:1), $R_F$=0.5. Yield: 4 g, 51.4%.

Step h) tert-Butyl 3,3-difluoro-1-(hydroxymethyl)cyclobutylcarbamate (BB2-h)

To a ice cooled solution of compound BB2-g (4 g, 0.0143 mol) in dry THF (100 mL) was slowly added a solution of 2M lithium borohydride (30 mL) and the mixture was allowed to warm up to room temperature. The mixture was stirred for three hours at room temperature. Ice water and 5% citric acid were added and the mixture was extracted three times with DCM. The organic phase was dried ($Na_2SO_4$), filtered and evaporated under reduced pressure which gave the title compound. TLC system petroleum ether: ethyl acetate (1:1), $R_F$=0.3. Yield: 3.1 g, 91%.

Step i) tert-Butyl 3,3-difluoro-1-formylcyclobutylcarbamate (BB2-i)

To a solution of compound BB2-h (3.1 g, 0.0130 mol) in dry DCM (100 mL) was added Dess Martin Period inane (19.9 g, 0.0470 mol) and the mixture was stirred for three hours at room temperature. Ethyl acetate (200 mL) was added and the organic phase was washed twice with 10% sodium thiosulphate solution, twice with 0.5 M NaOH and with brine. The organic phase was dried and evaporated under reduced pressure. The residue was purified by silica gel chromatography with hexane/ethyl acetate as eluent which gave the title compound. TLC system; petroleum ether: ethyl acetate (1:1), $R_F$=0.4. Yield: 2.7 g, 87%.

Step j) tert-Butyl 1-(2-(tert-butylamino)-1-hydroxy-2-oxoethyl)-3,3-difluorocyclobutylcarbamate (BB2-j)

To a ice cooled solution of compound BB2-i (1.5 g, 0.0064 mol) in dry DCM (100 mL) was added tert-butylisocyanate (0.81 g, 0.009 mol) and pyridine (2.04 g, 0.027 mol). Trifluoroacetic acid (1.58 g, 0.015 mol) was added over a ten minutes period. The mixture was stirred for five hours at room temperature. Ethyl acetate was added and the organic phase was washed twice with 5% citric acid and brine. The organic phase was evaporated and dissolved in dioxane (50 mL). 1M LiOH solution (100 mL) was added and the mixture was stirred overnight at room temperature. 5% Citric acid was added and the mixture was extracted three times with ethyl acetate. The organic phase was washed with brine, dried (Na$_2$SO$_4$), filtered and evaporated under reduced pressure. The product was purified by silica gel chromatography with hexane/ethyl acetate as eluent. TLC system; Petroleum ether: ethyl acetate (1:1), $R_F$=0.4. Yield: 1.0 g, 46%.

Step k) 2-(1-(tert-Butoxycarbonylamino)-3,3-difluorocyclobutyl)-2-hydroxyacetic acid (BB2)

Compound BB2-j (1 g) was dissolved in 6N HCl (40 mL), and heated to reflux for 24 h after which TLC showed that the reaction had reached completion. The reaction mixture was concentrated in vacuo and residue was dissolved in THF; H$_2$O (7; 3, 50 mL), and TEA (1.8 mL, 0.012 mol) and Boc anhydride (2.6 g, 0.012 mol) were both added. The mixture was stirred at RT for 8 h when TLC confirmed the reaction had reached completion. The reaction mixture was concentrated in vacuo and the residue was purified by column chromatography using 5% methanol in chloroform which gave the title compound. TLC system; MeOH: CHCl$_3$ (1:9), $R_F$=0.4. Yield: 0.6 g, 72%.

$^{1H}$NMR (400 MHz, d$_6$-DMSO) δ 7.30 (br s, 1H), 4.11 (s, 1H), 2.90 (br m, 2H), 2.61 (br m, 2H), 1.35 (s, 9H); ms ES$^+$ m/z 281 (100%).

Preparation of Building Block 3 (BB3), a P1 Building Block

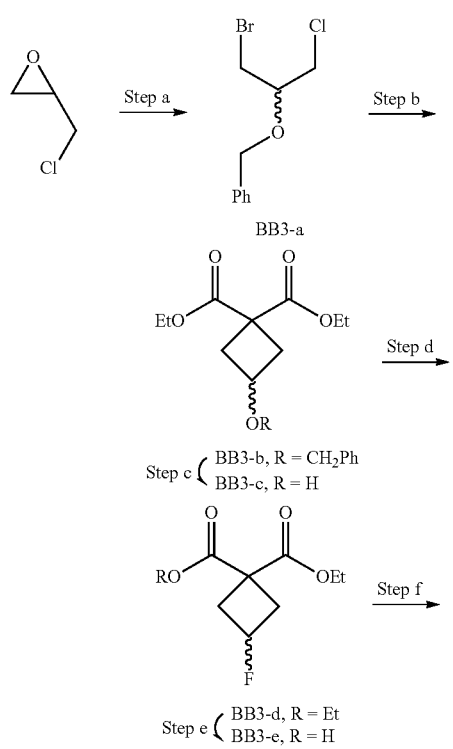

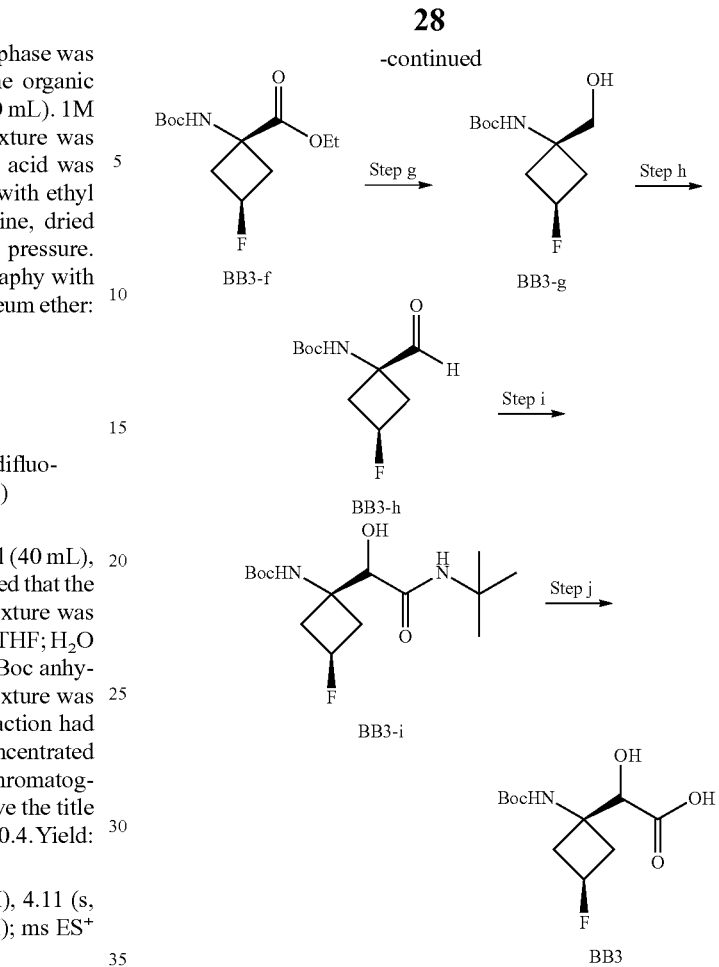

Step a) ((1-Bromo-3-chloropropan-2-yloxy)methyl)benzene (BB3-a)

A mixture of benzyl bromide (46.0 g, 0.269 mol) and epichlorohydrin (24.9 g, 0.269 mol) and mercurous chloride (0.04 g, 0.085 mmol) was heated for 12 h at 150° C. The crude product was purified by column chromatography (silica gel 60-120 mesh, eluent 1% EtOAc in pet ether) which afforded the title compound as a viscous liquid (50 g, yield 70%). TLC system: 10% EtOAc in pet ether, $R_f$=0.6.

Step b) Diethyl 3-(benzyloxy)cyclobutane-1,1-dicarboxylate (BB3-b)

In a three-neck flask equipped with stirrer, additional funnel and reflux condenser was place NaH (4.6 g, 0.192 mol) in dry dioxane (150 mL). To this stirred reaction mixture, diethyl malonate (30.75 g, 0.192 mol) was added drop-wise over 30 min After the addition was complete, compound BB3-a (50 g, 0.19 mol) was added drop-wise over a period of 30 min The reaction mixture was refluxed for 24 h. After cooling to room temperature, NaH (4.6 g, 0.192 mol) and dry dioxane (40 mL) was added to the reaction mixture and further heated to reflux for another 48 h. The solvent was partially removed under reduced pressure and the mixture was treated with water (150 mL). The product was extracted with diethyl ether (3×100 mL), the organic layer was washed with brine and dried over anhydrous Na$_2$SO$_4$. Solvent was concen-

Step c) Diethyl 3-hydroxycyclobutane-1,1-dicarboxylate (BB3-c)

To a solution of compound BB3-b (33 g, 0.108 mol) in EtOH (300 mL) was added 10% palladium on charcoal (10 g) and the mixture was hydrogenated for 48 h with 50 psi pressure at room temperature. The catalyst was removed by filtration through a celite bed and washed thoroughly with EtOAc. The solvent was removed under reduced pressure. The product was purified by silica gel chromatography (silica gel 60-120 mesh, eluent 20% EtOAc in pet ether) which afforded the title compound as a viscous liquid (12 g, yield 51%). TLC system: 30% EtOAc in pet ether, $R_f$=0.3.

Step d) Diethyl 3-fluorocyclobutane-1,1-dicarboxylate (BB3-d)

Compound BB3-c (0.8 g, 0.0037 mol) was dissolved in dry DCM (16 mL) and cooled to 0° C. DAST (1.8 g, 0.011 mol) was added drop-wise to the cold solution. The reaction mixture was warmed to room temperature stirred for 12 h. The reaction mixture was quenched with cold saturated $NaHCO_3$ solution. The crude product was extracted with DCM (100 mL). The organic layer was washed with 10% $NaHCO_3$ solution, water followed by brine and dried over anhydrous $Na_2SO_4$. Solvent was concentrated in vacuum and the crude product was purified by column chromatography (silica gel 60-120 mesh, eluent 1-2% EtOAc in pet ether) which afforded the title compound as a pale yellow liquid (460 mg, yield 57%). TLC system: 10% EtOAc in pet ether, $R_f$=0.4.

Step e) 1-(Ethoxycarbonyl)-3-fluorocyclobutanecarboxylic acid (BB3-e)

Compound BB3-d (0.46 g, 0.0021 mol) was dissolved in ice cooled 0.5M potassium hydroxide solution in EtOH (4.2 mL) and water (1.4 mL). The mixture was stirred at room temperature overnight. Water was added and most of the ethanol was removed under reduced pressure. The mixture was acidified with 2N HCl and extracted with EtOAc (3×50 mL). The organic phase was dried over anhydrous $Na_2SO_4$. Solvent was concentrated in vacuum to afford the crude title compound (0.35 g, crude) which was used as such for the next step. TLC system: 50% EtOAc in pet ether, $R_f$=0.3.

Step f) Ethyl 1-(tert-butoxycarbonylamino)-3-fluorocyclobutanecarboxylate (BB3-f)

To a solution of compound BB3-e (0.35 g, 0.0018 mol) in dry dioxane (6 mL) was added tert-butanol (1.8 mL), diphenyl phosphoryl azide (0.56 g, 0.002 mol) and triethylamine (0.2 g, 0.002 mol) and the mixture was refluxed for 5 h. After completion of the reaction, EtOAc (60 mL) was added to the reaction mixture and the organic layer was washed with 5% citric acid (2×20 mL) followed by saturated $NaHCO_3$ (50 mL). The organic solvent was evaporated under reduced pressure. To the residue EtOAc (100 mL) was added and the organic layer was washed with brine and dried over anhydrous $Na_2SO_4$. Solvent was concentrated in vacuum and the crude product was purified by column chromatography (silica gel 60-120 mesh, eluent 5-10% EtOAc in pet ether) which afforded the title compound as white crystals (0.27 g, yield 56%). TLC system: 20% EtOAc in pet ether, $R_f$=0.4.

Step g) tert-Butyl 3-fluoro-1-(hydroxymethyl)cyclobutylcarbamate (BB3-g)

To a ice cooled solution of compound BB3-f (0.27 g, 0.001 mol) in dry THF (10 mL) was slowly added a solution of 2M lithium borohydride (2 mL, 0.004 mol) and the mixture was allowed to warm up to room temperature. The mixture was stirred for 3 h at room temperature. The reaction mixture was quenched with ice water (2 mL) and 5% citric acid (5 mL) and the crude product was extracted with DCM (2×50 mL). The organic layer was washed with brine and dried over anhydrous $Na_2SO_4$. Solvent was concentrated in vacuum and the crude product was purified by column chromatography (silica gel 60-120 mesh, eluent 15-18% EtOAc in pet ether) which afforded the title compound as white solid (90 mg, yield 39%). TLC system: 50% EtOAc in pet ether, $R_f$0.5.

Step h) tert-Butyl 3-fluoro-1-formylcyclobutylcarbamate (BB3-h)

To a degassed solution of compound BB3-g (90 mg, 0.0004 mol) in dry DCM (4.5 mL) was added Dess-Martin Periodinane (0.21 g, 0.0005 mol) and the mixture was stirred for 3 h at room temperature. EtOAc (30 mL) was added and the organic layer was washed with 10% sodium thiosulphate solution (2×10 mL), 0.5 M NaOH (20 mL) and with brine. The organic layer was dried over anhydrous $Na_2SO_4$. Solvent was concentrated in vacuum and the crude product was purified by column chromatography (silica gel 60-120 mesh, eluent 10-15% EtOAc in pet ether) which afforded the title compound as a white crystalline solid (75 mg, yield 87%).TLC system: 20% EtOAc in pet ether, $R_f$=0.4.

Step i) tert-Butyl 1-(2-(tert-butylamino)-1-hydroxy-2-oxoethyl)-3-fluorocyclobutylcarbamate (BB3-i)

To an ice cooled solution of compound BB3-h (1.3 g, 0.0059 mol) in dry DCM (25 mL) was added tert-butyl isocyanide (0.75 g, 0.0089 mol) and dry pyridine (2.6 mL). Trifluoroacetic acid (0.9 mL, 0.0118 mol) was added over a period of ten minutes maintaining the temperature at 0° C. The reaction mixture was slowly warmed to room temperature and stirred for 16 h. EtOAc (50 mL) was added and the organic phase was washed twice with 5% citric acid and brine. The organic phase was evaporated and the crude product was dissolved in THF (25 mL). 1M LiOH solution in MeOH—$H_2O$ (3:2v/v) (2.6 mL) was added and the mixture was stirred for 2 h at room temperature. The reaction mixture was quenched with 5% citric acid and the mixture was extracted with ethyl acetate (2×25 mL). The organic layer was washed with brine and dried over anhydrous $Na_2SO_4$. Solvent was evaporated in vacuum and to afford the title compound which was pure enough to be used in the next step (1.6 g, yield 84%). TLC system: 20% EtOAc in pet ether, $R_f$=0.3.

Step j) 2-(1-(tert-Butoxycarbonylamino)-3-fluorocyclobutyl)-2-hydroxyacetic acid (BB3)

Compound BB3-i (1.6 g, 0.005 mol) was refluxed with 6N HCl (60 mL) for 16 h until the amide hydrolysis was complete. The solvent was evaporated under reduced pressure and co-evaporated several times with water. The product was dissolved in THF:H₂O (7:3 v/v, 50 mL), cooled to 0° C. and Et₃N (2.1 mL, 0.015 mol) was added followed by di-tert-butyl dicarbonate (2.18 g, 0.01 mol). The mixture was stirred at room temperature overnight (pH was monitored in a regular interval and kept ~11 throughout the reaction). The reaction mixture was neutralized with 1N HCl and the product was extracted with EtOAc (2×50 mL). The organic layer was washed with brine and dried over anhydrous Na₂SO₄. The solvent was evaporated under reduced pressure followed by purification by column chromatography (silica gel 60-120 mesh, eluent 5% MeOH in CHCl₃) which afforded the title P1 building block as a solid (0.65 g, yield 50%). TLC system: 30% MeOH in CHCl₃, R_f=0.3.

¹H NMR (400 MHz, d₆-DMSO) δ 7.01 (br s, 1H), 5.16 (br m, 1H), 4.97 (br m, 1H), 2.49 (br m, 5H), 1.36 (s, 9H); ms ES⁺ m/z 262 (100%).

Building Block 4 (BB4), a P1 Building Block

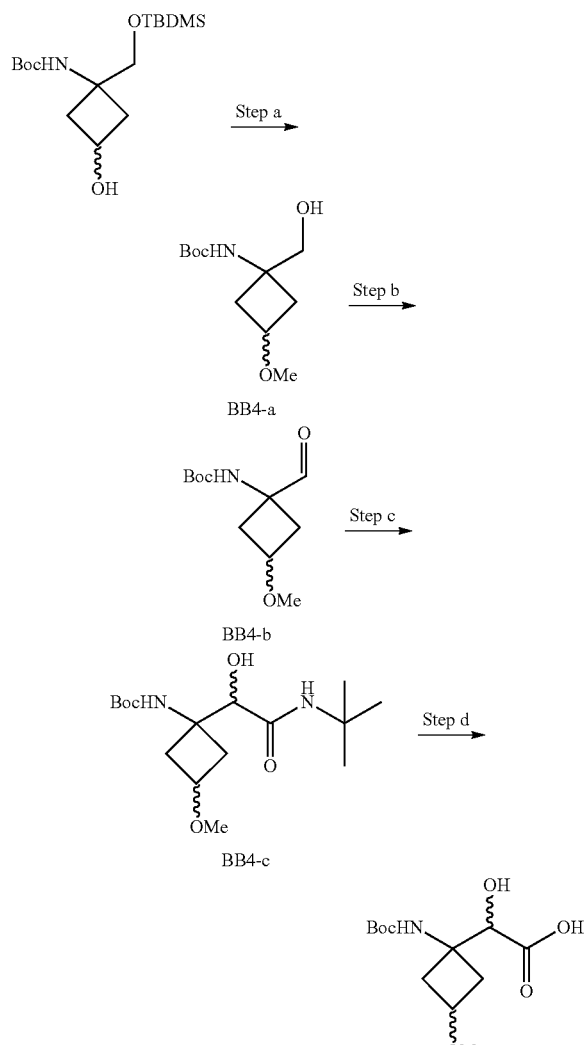

Step a) tert-butyl 1-(hydroxymethyl)-3-methoxycyclobutylcarbamate (BB4-a)

500 mg (1.51 mmol) of tert-butyl 1-((tert-butyldimethylsilyloxy)methyl)-3-hydroxycyclobutylcarbamate (prepared by reduction of ethyl-1[[tert-butyloxy)carbonyl]amino]-3-hydroxycyclobutane-1-carboxylate as described in J. Med. Chem., 1990 33(10) 2905-2915) and proton sponge (N,N,N', N' tetramethylnapthalene-1,8 diamine) (1.63 g, 6.04 mmol) were dissolved in DCM (18 mL), cooled down to 0° C., and 447 mg (3.02 mmol) of trimethyloxonium borontetrafluoride was added in one portion as a solid under vigorous stifling. The reaction mixture was stirred for 3 h and diluted with DCM (50 mL) and brine (20 mL), added under vigorous stifling. The organic phase was washed with sodium bicarbonate, brine, dried over sodium sulphate, evaporated and purified on short silica column (DCM as an eluent). The resulting product was dissolved in THF (5 mL), and a solution of tetrabutylammonium fluoride in THF (1M, 4.5 mL) was added, and the reaction was stirred at room temperature for 4.5 h. The reaction was monitored by TLC and once deemed to have reached completion, it was absorbed onto silica and purified on silica (EtOAc-hexane 1:1 to neat EtOAc) to give the title compound (251 mg, 72%). LC/MS 232 (M+1).

Step b) tert-Butyl 1-formyl-3-methoxycyclobutylcarbamate (BB4-b)

Alcohol BB4-a was dissolved in DCM (20 mL) and Dess-Martin reagent was added in one portion. The reaction was stirred for 2.5 hours. Once the reaction was deemed to have reached completion, it was diluted with 50 mL of DCM and 20 mL of 10% Na₂S₂O₃ was added. The mixture was stirred, washed with sodium bicarbonate, brine, and the organic phase was dried over sodium sulphate. Purification on silica (EtOAc-hexane 1:1 to neat EtOAc) gave the title compound (500 mg, 59%).

Step c) [1-(tert-Butylcarbamoyl-hydroxymethyl)-3-methoxycyclobutyl]-carbamic acid tert-butyl ester (BB4-c)

Aldehyde BB4-b, 4.45 mmol, was dissolved in dry DCM (11 mL). Pyridine (2 mL) was added under stirring conditions, followed by adding tert-butyl isocyanide (6.68 mmol). The reaction was placed in an ice-bath and TFA (0.68 mL) was added dropwise during 20 min The reaction mixture was stirred overnight. The reaction was then deemed to have reached completion and the solvent was removed under reduced pressure. The residue was redissolved in EtOAc and washed with 1 M HCl (2×), sodium bicarbonate, brine, and the organic phase dried over sodium sulphate and evaporated. The remaining residue was dissolved in dioxane and stirred with lithium hydroxide solution overnight and neutralized with citric acid. The product was extracted with EtOAc from the resulting solution and purified on silica (EtOAc-hexane 1:3 to 1:1) which gave 850 mg of the title compound (58%) TLC: rf=0.61(EtOAc:hexane 1:1).

Step d) (1-tert-Butoxycarbonylamino-3-methoxy-cyclobutyl)-hydroxy-acetic acid (BB4)

The amide BB4-c (850 mg, 2.57 mmol) was refluxed with 6N HCl (60 mL) for 16 h until the amide hydrolysis was complete. The solvent was evaporated under reduced pressure and co-evaporated with water. The product was dissolved in THF:H₂O (7:3 v/v, 50 mL), cooled to 0° C. and Et₃N (1.4 mL, 10.2 mmol) was added followed by di-tert-butyl dicarbonate (2.25 g, 10.2 mol). The mixture was stirred at room temperature overnight. The reaction mixture was washed with EtOAc followed by acidifying to pH3 with 1N HCl and extracted with EtOAc (2×50 mL). The organic layer Building Block 5 (BB5), a P2 Building Block

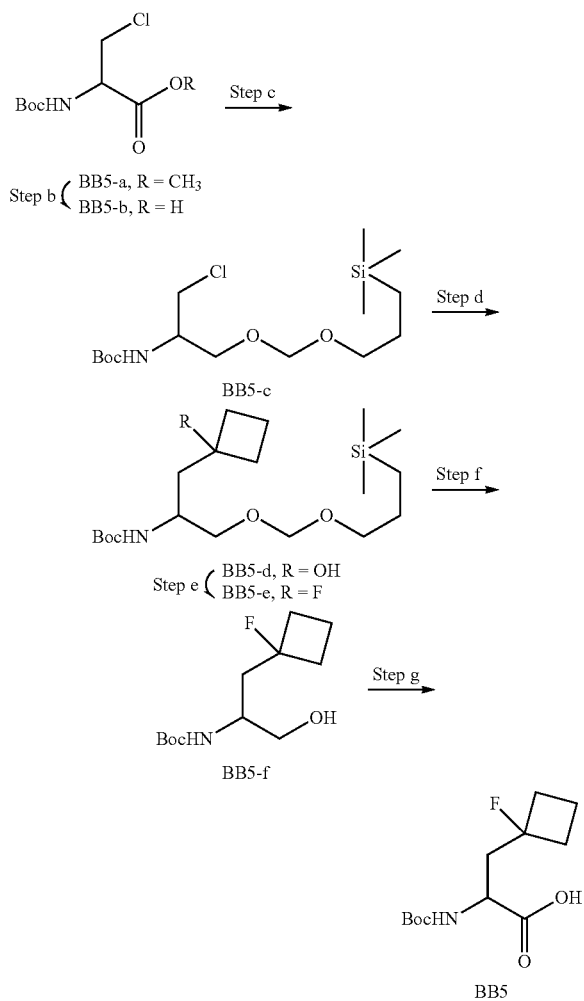

Step a) 2-tert-Butoxycarbonylamino-3-chloro-propionic acid methyl ester (BB5-a)

A solution of triphenylphosphine (65.8 g, 0.251 mol)) and hexachloroethane (59.4 g, 0.251 mol) in dichloromethane (850 mL) was added in one portion to a solution of N-Boc-serine methyl ester (50 g, 0.228 mol) in dichloromethane (170 mL) under argon atmosphere. The reaction mixture was stirred at room temperature for 2 h and then the reaction was quenched with a saturated solution of NaHCO$_3$ (150 mL). The organic product was extracted with dichloromethane (2×300 mL) and the combined organic layers was washed with brine (300 mL) and dried over anhydrous sodium sulphate. The solution was concentrated under reduced pressure and then triturated with Et$_2$O (500 mL). After filtration and evaporation of the solvent, the crude product was purified by chromatography on a silica column eluted with 6-8% EtOAc in pet. ether) which gave the title compound (42 g, 78%).

Step b) (2-Chloro-1-hydroxymethyl-ethyl)-carbamic acid tert-butyl ester (BB5-b)

Lithium borohydride (4.3 g, 0.195 mol) was added in portions to a stirred solution of BB5-a (42 g, 0.177 mol) in EtOH-THF 9:1 at 0° C. under argon atmosphere. The reaction was stirred for 8 h at room temperature then quenched with a saturated solution of ammonium chloride (20 mL). The product was extracted with EtOAc (2×300 mL). The combined organic layers was washed with brine (300 mL) and dried over anhydrous sodium sulphate. The solvent was evaporated under reduced pressure and the afforded crude product was purified by chromatography on a silica column eluted with 15% EtOAc in pet. ether, which gave the title compound (27.5 g, 74%).

Step c) [2-Chloro-1-(2-trimethylsilanyl-ethoxymethoxymethyl)-ethyl]-carbamic acid tert-butyl ester (BB5-c)

(2-Chloromethoxy-ethyl)-trimethyl-silane (26.18 g, 0.157 mol) was added drop-wise to a stirred solution of compound BB5-b (27.5 g, 0.131 mol) and N,N-diisopropylethylamine (27.4 mL, 0.157 mol) in dichloromethane (350 mL) at 0° C. under argon atmosphere. The reaction was allowed to attain room temperature and stirred for 18 h. The reaction mixture was concentrated under vacuum and then diluted with EtOAc (150 mL). The product was extracted with EtOAc (2×200 mL) and the organic layer was washed with brine (100 mL) and dried over anhydrous sodium sulphate. The solvent was evaporated under reduced pressure and the afforded crude product was purified by chromatography on silica a column eluted with 5% EtOAc in pet. ether, which gave the title compound (25.5 g, 57%).

Step d) [2-(1-Hydroxy-cyclobutyl)-1-(2-trimethylsilanyl-ethoxymethoxymethyl)-ethyl]-carbamic acid tert-butyl ester (BB5-d)

n-BuLi (10 mL, 0.016 mol, 1.6 M solution in hexanes) was added drop-wise to a stirred solution of compound BB5-c (2 g, 5.88 mmol) in THF (170 mL) at −78° C. under argon atmosphere. The stirring was continued for 15 min, followed by drop-wise addition of LiNp (104 mL, 0.42 M solution in THF, 0.044 mol) over 5 min. The dark solution was stirred at −78° C. for 1 h and then cyclobutanone (0.88 mL, 11.77 mmol) was added drop-wise. The reaction mixture was stirred at −78° C. for 16 h then quenched with a saturated solution of NH$_4$Cl (50 mL) and allowed to warm to room temperature. The reaction was diluted with ether (100 mL) and a saturated solution of NH$_4$Cl (10 mL). The layers were separated and the aqueous layer was extracted with ether (2×100 mL). The combined organic layers was dried (Na$_2$SO$_4$) and the solvent was evaporated under reduced pressure. The crude product was purified by chromatography on a silica column eluted with heptane:ether 3:2, which gave the title compound (1.54 g, 70%,).

Step e) [2-(1-Fluoro-cyclobutyl)-1-(2-trimethylsilanyl-ethoxymethoxymethyl)-ethyl]-carbamic acid tert-butyl ester (BB5-e)

BB5-d (0.5 g, 1.33 mmol), 50% Deoxofluor in THF (excess) and pyridine (excess) were mixed in DCM (10 mL). The resulting mixture was stirred at rt over night. The reaction mixture was washed with 10% citric acid (aq) and sat. NaHCO$_3$ (aq). The organic phase was dried (Na$_2$SO$_4$) and evaporated. The afforded crude product was purified by chromatography on a silica column using hexane:EtOAc (7:1 to 2:1) as eluent, which gave the title compound (192 mg, 38%).

Step f) [2-(1-Fluoro-cyclobutyl)-1-hydroxymethyl-ethyl]-carbamic acid tert-butyl ester (BB5-f)

A solution of BB5-e (192 mg, 0.51 mmol) in 0.1 M HCl in MeOH (20 mL) was stirred for 3 hours, then triethylamine (1 mL) was added and the solution was concentrated. The afforded crude product was purified by chromatography on a silica column using hexane:EtOAc (2:1) as eluent, which gave the title compound (69.3 mg, 55%) as a white solid.

Step g) 2-tert-Butoxycarbonylamino-3-(1-fluoro-cyclobutyl)-propionic acid (BB5)

BB5-f (69 mg, 0.279 mmol) and pyridine dichromate (1.15 g, 3.05 mmol) were dissolved in dry DMF (5 mL). After five hours H$_2$O (15 mL) was added and the product was extracted with DCM (3×20 mL). The combined organic layers was dried (Na$_2$SO$_4$) and evaporated. The crude was purified by chromatography on a silica column using hexane:EtOAc (1:1) followed by EtOH (100%) as eluent. This afforded the title compound as a white solid (22.3 mg, 31%), 262.4 [M+H]$^+$.

Building Block 6 (BB6), a P1 α-hydroxy amide

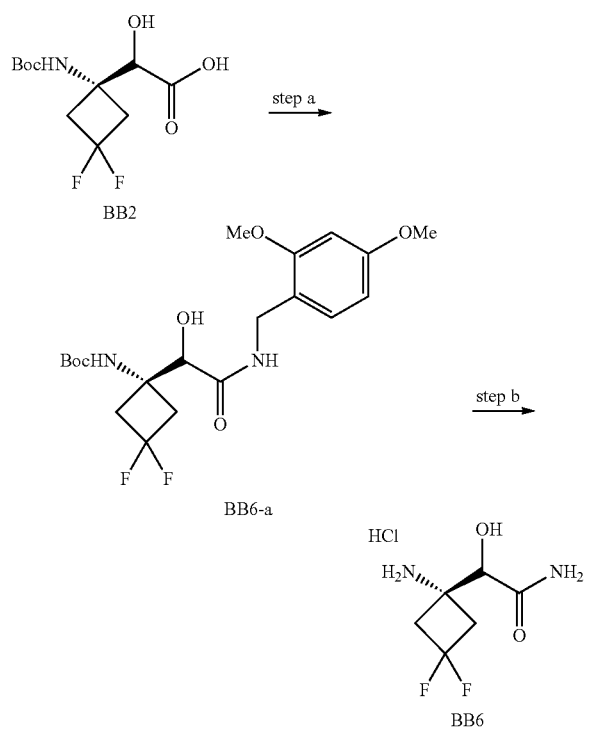

Step a) (S)-tert-butyl(1-(2-((2,4-dimethoxybenzyl)amino)-1-hydroxy-2-oxoethyl)-3,3-difluorocyclobutyl)carbamate (BB6-a)

α-Hydroxy acid BB2 (1.5 g, 5.3 mmol) and 2,4-dimethoxybenzylamine (809 mg, 5.35 mmol) was dissolved in CH$_2$Cl$_2$ (15 ml) and DMF (3 ml). HATU (2.066 g, 5.43 mmol) was added followed by diisopropylethylamine (948 μl, 5.4 mmol) and the mixture was stirred at 22° C. over night. The mixture was diluted with CH$_2$Cl$_2$ and washed with 0.1 M HCl (aq) ×2 and then dried (Na$_2$SO$_4$), filtered and concentrated. The residue was purified by silica using p-ether/EtOAc (8:2→6:4) which gave the title compound (2.25 g, 5.22, 98% yield) mmol as a clear oil.

Step b) (S)-2-(1-amino-3,3-difluorocyclobutyl)-2-hydroxyacetamide Hydrochloride salt (BB6)

Compound BB6-a (342 mg, 0.79 mmol) was dissolved in a solution of TFA:CH$_2$Cl$_2$ 75:25 (3 mL ml) and 5% triethylsilane (150 μL). The mixture was heated to 110° C. for 20 min in a micro wave reactor. The mixture was then poured into an ice/1M HCl (aq) mixture and washed with CH$_2$Cl$_2$×3 whereafter the acidic water phase was concentrated on a rotavapor at 35° C. which gave the title compound as hydrochloride salt [M+1]$^+$=180.8

Building Block 7 (BB7), a P1 α-hydroxyamide

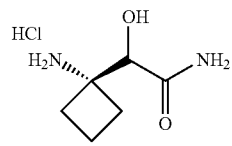

(S)-2-(1-aminocyclobutyl)-2-hydroxyacetamide (BB7)

The title compound was prepared from α-hydroxy acid BB1 according to the procedure described in BB6 steps a and b.

Building Block 8, a P1 α-hydroxyamide

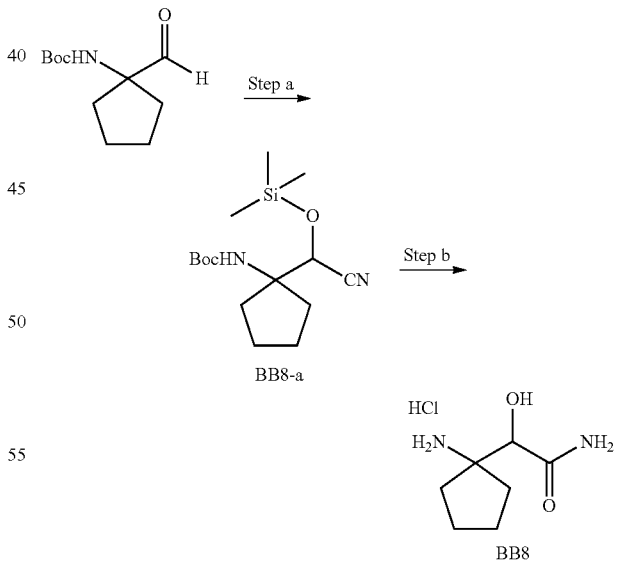

Step a) tert-butyl(1-(cyano((trimethylsilyl)oxy)methyl)cyclopentyl)carbamate (BB8-a)

To a solution of N-Boc-cycloleucinal (1.035 g, 4.85 mmol) in dry DCM (20 ML) was added TMS-CN (645 μL, 4.85 mmol), and the solution was stirred for 72 h, then quenched with saturated aq. NaHCO₃ and extracted with DCM. The organic layer was dried over Na2SO4 anhydrous, concentrated and the residue purified using flash silica column with n-hexane:EtOAc 0-50% to give the title compound as a colourless oil (1.36 g). [M+1]⁺=312.8.

Step b) 2-(1-aminocyclopentyl)-2-hydroxyacetamide (BB8)

Cyano compound BB8-a (420.7 mg, 1.348 mmol) was dissolved in a solution of formic acid: HCl 1:1 (6 mL) and the resulting solution was stirred for 16 h. Acetonitrile was added and the solution concentrated, and co-evaporated with toluene to give the titled amine as hydrochloride salt. [M+1]⁺=158.9.

Building Block 9, a P1 α-hydroxyamide

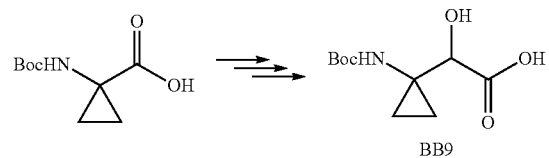

2-(1-((Tert-butoxycarbonyl)amino)cyclopropyl)-2-hydroxyacetic acid (BB9)

The title compound was prepared in 29% overall yield from N-Boc-1-aminocyclopropanecarboxylic acid (5.03 g, 25.0 mmol), according to the procedure described for the preparation of BB1.

EXAMPLE C1

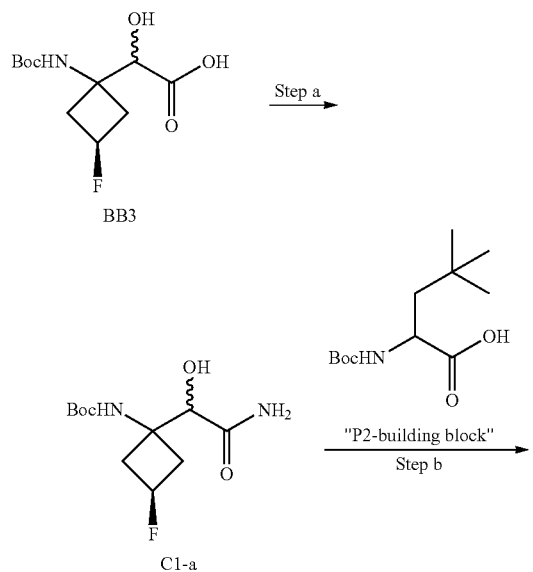

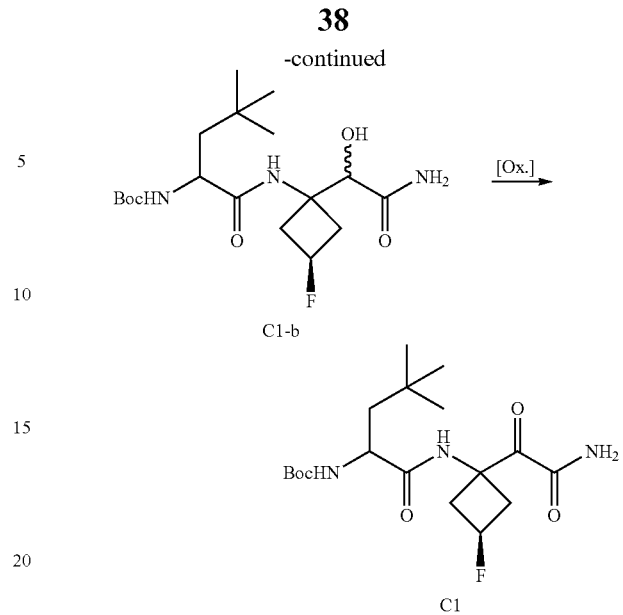

Step a) Tert-butyl(1r,3r)-1-(2-amino-1-hydroxy-2-oxoethyl)-3-fluorocyclobutylcarbamate (C1-a)

Potassium carbonate (147.5 mg, 1.06 mmol) was added to a solution of BB3 (254 mg, 0.96 mmol) in DMF (5 mL) followed by addition of methyl iodide (72 μL, 1.15 mmol). The reaction mixture was stirred at room temperature for 2.5 h and then partitioned between DCM and aq. NaHCO₃ (sat.). The phases were separated and the organic layer was washed with water, dried (Na₂SO₄) and concentrated. MS m/z 277.9 (M+H)⁺. The methyl ester crude residue formed was dissolved in a saturated solution of NH3 in methanol (10 mL) then heated at 60° C. for 5 days and concentrated which gave the title compound pure enough to be used in the next step without further purification. MS m/z 262.9 (M+H)⁺.

Step b) Tert-butyl(S)-1-((1r,3S)-1-(2-amino-1-hydroxy-2-oxoethyl)-3-fluorocyclobutylamino)-4,4-dimethyl-1-oxopentan-2-ylcarbamate (C1-b)

The Boc-protected amine C1-a (0.48 mmol), was treated with HCl (4M in dioxane, 5 mL) for 3 h whereafter the reaction mixture was concentrated. The resulting hydrochloride salt of the amine was added to a cold solution of Boc-β-tBu-Ala-OH (129.5 mg, 0.53 mmol) and HATU (200 mg, 0.53 mmol) in anh. DMF (4 mL) was added at 0° C., followed by addition of DIEA (335 μL, 1.92 mmol). The reaction mixture was stirred at room temperature over night, and then concentrated. Purification by flash column chromatography (EtOAc/iso-Hexane, 0:1-7:3) gave the title compound (0.130 g, 70%). MS m/z 390.0 (M+H)⁺.

Step c) Tert-butyl(S)-1-((1r,3S)-1-(2-amino-2-oxoacetyl)-3-fluorocyclobutylamino)-4,4-dimethyl-1-oxopentan-2-ylcarbamate (C1)

Dess-Martin periodinane (0.301 g, 0.71 mmol) was added to a solution of the α-hydroxy amide C1b (0.184 g, 0.47 mmol) in DCM (5 ml). The reaction mixture was stirred at room temperature over night and quenched with 10% aq. Na₂S₂O₃ and aq. NaHCO₃ (sat.). The phases were separated and the organic layer was dried (Na₂SO₄) and concentrated. Purification by flash column chromatography (EtOAc/iso- Hexane, 0:1-1:0) gave the title compound (0.130 g, 67%). A small portion was further purified by RP-LC-MS (0.1% NH$_4$OH in acetonitrile-0.1% aq. NH$_4$OH, 40-65% over 9 min.) MS m/z 386.5 (M−H)⁻.

EXAMPLES C2-C4

The compounds illustrated in the table below were prepared analogously to the procedure described in Example C1 using the appropriate P1 and P2 building blocks, followed by oxidation to the end product α-keto amide.

TABLE C1

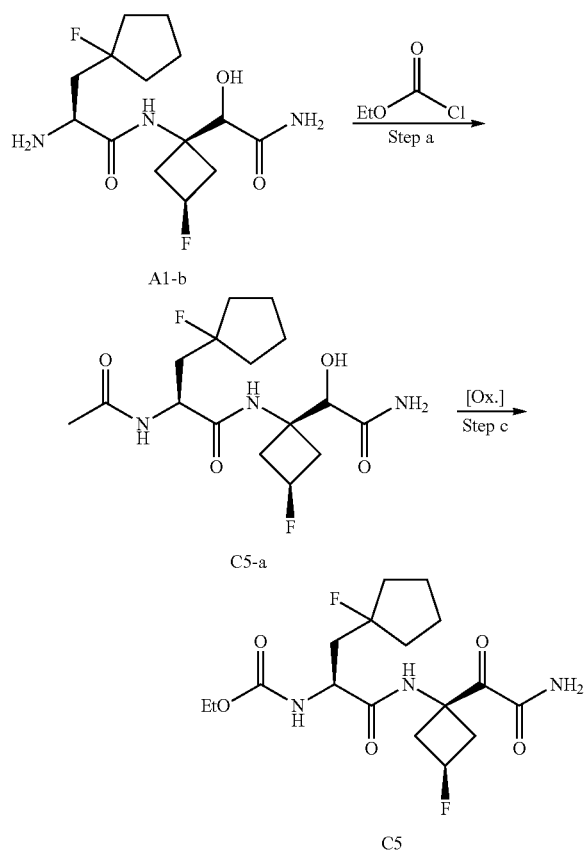

| Ex. | R³ | R²ᵃ | R²ᵇ | [M + H]⁺ |
|---|---|---|---|---|
| C2 | 2,2-dimethylbutyl | H | H | 369.9 |
| C3¹ | 1-fluorocyclopentylmethyl | F | H | 417.9 |
| C4¹ | 1-methylcyclopentylmethyl | H | H | 395.9 |

¹Removal of the Boc group in step b was performed using TFA/H₂O/TIS 9.5/0.25/0.25.

EXAMPLE C5

[1-[1-(Carbamoyl-hydroxy-methyl)-3-fluoro-cyclobutylcarbamoyl]-2-(1-fluoro-cyclopentyl)-ethyl]-carbamic acid ethyl ester (C5-a)

Diisopropylethylamine (0.087 mL, 0.5 mmol) and ethyl chloroformate (0.024 mL, 0.25 mmol) were added to a stirred solution of the amine A1-b, 2-amino-N-[1-(carbamoyl-hydroxy-methyl)-3-fluoro-cyclobutyl]-3-(1-fluorocyclopentyl)-propionamide (0.23 mmol) in DMF. After 15 min sat. aq. NaHCO$_3$ and DCM were added and the organic layer was collected and concentrated and purified on flash silica gel column using DCM-MeOH 0-10% which gave the title compound (62 mg) [M+1]⁺391.9.

[1-(1-Aminooxalyl-3-fluoro-cyclobutylcarbamoyl)-2-(1-fluoro-cyclopentyl)-ethyl]-carbamic acid ethyl ester (C5)

A solution of Dess Martin periodinane (75 mg, 0.177 mmol) in dichloroethane (5 mL) was added to solid [1-[1-(carbamoyl-hydroxy-methyl)-3-fluoro-cyclobutylcarbamoyl]-2-(1-fluoro-cyclopentyl)-ethyl]-carbamic acid ethyl ester (62 mg). After stirring for 2 h, NaHCO$_3$ (aq) was added, the layers were separated and the organic layer was concentrated. The afforded crude product was purified on a prep RP HPLC-UV/MS, which gave the title compound (14 mg). [M+1]⁺389.9.

EXAMPLE C6

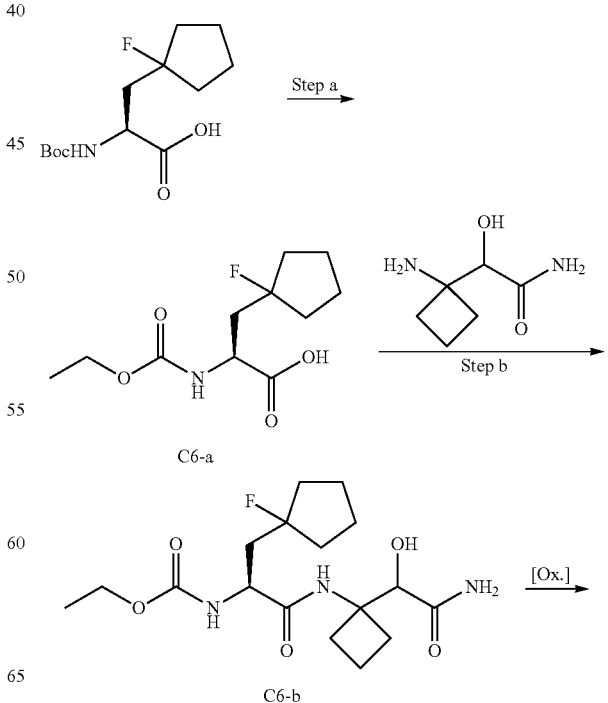

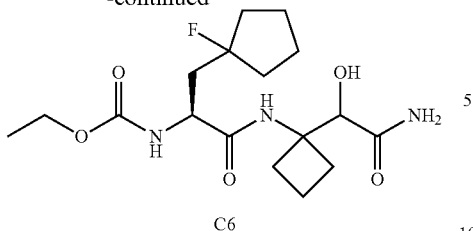

C6

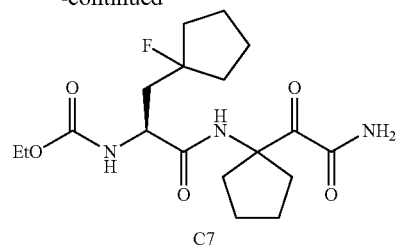

C7

Step a) 2-Ethoxycarbonylamino-3-(1-fluorocyclopentyl)-propionic acid (C6-a)

2-tert-Butoxycarbonylamino-3-(1-fluorocyclopentyl)-propionic acid (200 mg, 0.73 mmol) was kept in 4M HCl in dioxane (3 mL) for 20 min The mixture was then freeze-dried and left under a vacuum for 2 h. The solid residue was dissolved in dioxane-H$_2$O 1:1 (12 mL). NaHCO$_3$ (2.18 mmol, 3 eq.) and then ethyl chloroformate (0.87 mmol 1.2 eq.) dissolved in of dioxane (1 mL) were added. The reaction mixture was stirred for 20 min until completed according LC-MS. The mixture was acidified by citric acid (10% aq.) to pH 5. The product was extracted with DCM (20 mL) and EtOAc (20 mL). The organic layers were combined, dried (MgSO$_4$) and concentrated. The afforded crude was used without further purification in the next step.

Step b) [1-[1-(Carbamoyl-hydroxy-methyl)-cyclobutylcarbamoyl]-2-(1-fluorocyclopentyl)-ethyl]-carbamic acid ethyl ester (C6-b)

HATU (84 mg, 0.22 mmol) and diisopropylethylamine (0.14 mL, 0.8 mmol) was added to a stirred and cooled (0° C.) solution of 2-ethoxycarbonylamino-3-(1-fluoro-cyclopentyl)-propionic acid (50 mg, 0.2 mmol) in DMF. After 5 min, crude HCl salt of 2-(1-amino-cyclobutyl)-2-hydroxy acetamide (290 mg, achieved from BB1 by removal of the Boc group) was added and the temperature raised to ambient. After 1 h sat. aq. NaHCO$_3$ and DCM were added and the organic layer collected, concentrated and purified on a flash silica column using DCM-MeOH 0-10% which gave the title compound (37 mg). [M+1]$^+$373.8.

Step c) [1-(1-Aminooxalyl-cyclobutylcarbamoyl)-2-(1-fluorocyclopentyl)-ethyl]-carbamic acid ethyl ester (C6)

The α-hydroxy amide C6-b (42 mg) was oxidized using Dess Martin periodinane as described in Ex. C5, which gave the title compound (1.7 mg). [M+1]$^+$=371.9.

EXAMPLE C7

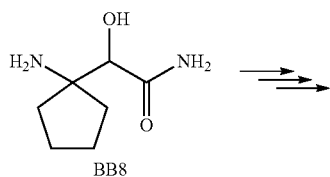

BB8

(S)-ethyl(1-((1-(2-amino-2-oxoacetyl)cyclopentyl)amino)-3-(1-fluorocyclopentyl)-1-oxopropan-2-yl) carbamate (C7)

BB8 was coupled to the P2-building block (S)-2-((tert-butoxycarbonyl)amino)-3-(1-fluorocyclopentyl)propanoic acid as described in Ex. C1 step b whereafter the P3 moiety was added by reaction with ethyl chloroformate as described in Ex. C5, which gave the title compound. [M+1]$^+$=386.8.

EXAMPLE C8

BB6

C8

Step a) (S)$_4$ ml-butyl(1-((1-(2-amino-2-oxoacetyl)-3,3-difluorocyclobutyl)amino)-3-(1-fluorocyclopentyl)-1-oxopropan-2-yl) carbamate (C8)

The amine BB6 was coupled to the P2-building block (S)-2-((tert-butoxycarbonyl)amino)-3-(1-fluorocyclopentyl) propanoic acid according to the method described in Ex. C1 step b. The afforded α-hydroxy amide (92 mg, 0.21 mmol) was dissolved in THF (2 mL) and DMSO (150 µL, 2.1 mmol)

was added followed by EDC hydrochloride salt (201 mg, 1 mmol). The solution was stirred for 15 min whereafter dichloroacetic acid (20 μL, 0.15 mmol) was added. The solution was stirred for 16 h, then diluted with DCM, and washed with aq. NaHCO₃ followed by citric acid (2% aq). The organic layer was separated and concentrated to dryness and the residue purified using flash silica column with DCM-MeOH 0-3% and further purified by prep LC-MS which gave the title compound (3 mg). [M+1]⁺=436.18.

The compounds in Table C2 were prepared according to the procedure described in Ex. C1, using the appropriate building blocks.

TABLE C2

| Ex. | R³ | n | [M + H]⁺ |
| --- | --- | --- | --- |
| C9 | cyclohexylmethyl | 2 | 396.0 |
| C10 | 1-fluorocyclopentylmethyl | 2 | 400.4 |
| C11 | 1-fluorocyclopentylmethyl | 1 | 386.4 |
| C12 | 1-methylcyclopentylmethyl | 1 | 382.4 |
| C13 | 1-fluorocyclopentylmethyl | 3 | 413.9 |

¹Removal of the Boc group in step b was performed using TFA/H₂O/TIS 9.5/0.25/0.25.

Compound C14 was prepared according to the procedure described in Ex. C5, using the appropriate building blocks.

| Ex. C14 | | [M + H]⁺ 386.4 |
| --- | --- | --- |

EXAMPLE A1

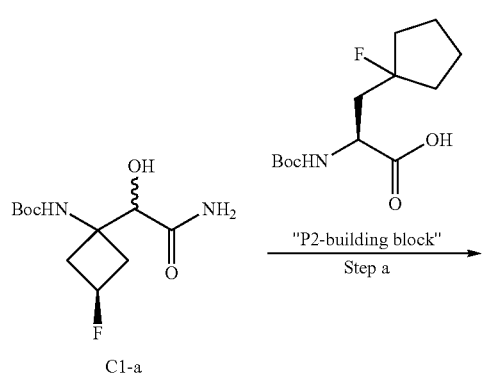

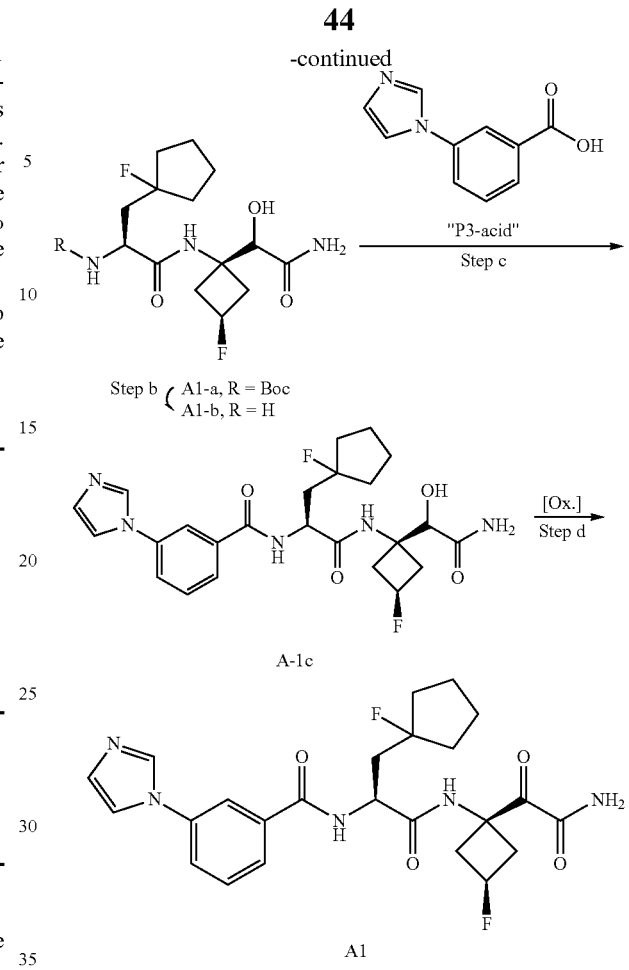

Step a) tert-butyl((S)-1-(((1r,3S)-1-((S)-2-amino-1-hydroxy-2-oxoethyl)-3-fluorocyclobutyl)amino)-3-(1-fluorocyclopentyl)-1-oxopropan-2-yl)carbamate (A1-a)

The title compound was prepared from the Boc-protected hydroxy amine C1-a by reaction with the "P2-building block" (S)-2-((tert-butoxycarbonyl)amino)-3-(1-fluorocyclopentyl) propanoic acid, according to the method described in Ex. C1 step b.

Step b) 2-Amino-N-[1-(carbamoyl-hydroxy-methyl)-3-fluoro-cyclobutyl]-3-(1-fluoro-cyclopentyl)-propionamide (A1-b)

The Boc-protected amine A1-a (0.223 mmol, 93 mg) was kept in a solution of dichloromethane containing 20% TFA/water/triisopropylsilane 9.5:0.25:0.25 (4 mL) for 30 min and then the solution was concentrated to dryness. DCE and 4M HCl in dioxane (1 mL) was added followed by concentration to dryness, which gave the title compound as the hydrochloride salt. [M+1]⁺=320.1.

Step c) N-[1-[1-(Carbamoyl-hydroxy-methyl)-3-fluoro-cyclobutylcarbamoyl]-2-(1-fluoro-cyclopentyl)-ethyl]-3-imidazol-1-yl-benzamide (A1-c)

To a stirred solution of the "P3-acid" 3-imidazol-1-yl-benzoic acid (47 mg, 0.25 mmol) in DMF (4 mL) was added HATU (95 mg, 0.25 mmol) and diisopropylamine (0.147 mL, 1 mmol). After 2 min the amine A1-b (0.22 mmol) was added. After 2 h a saturated aqueous solution of NaHCO₃ (3 mL) was added and the mixture was extracted with DCM (5 mL). The organic phase was concentrated and the residue purified using flash silica column with DCM-MeOH 0-10%, which gave the title compound (10 mg). [M+1]⁺=489.9.

Step d) N-[1-(1-Aminooxalyl-3-fluoro-cyclobutyl-carbamoyl)-2-(1-fluoro-cyclopentyl)-ethyl]-3-imidazol-1-yl-benzamide (A1)

A solution of Dess Martin periodinane in dichloromethane (5 mL) was added to the α-hydroxy amide A1-c (10 mg). After stirring for 2 h, NaHCO₃ (aq) was added, the layers were separated and the organic layer was concentrated. The afforded crude product was purified on a prep RP HPLC-UV/MS, which gave the title compound (1.5 mg). [M+1]⁺487.8.

EXAMPLE A2

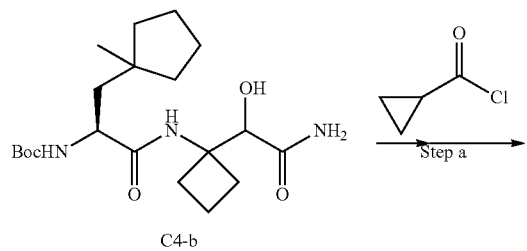

C4-b

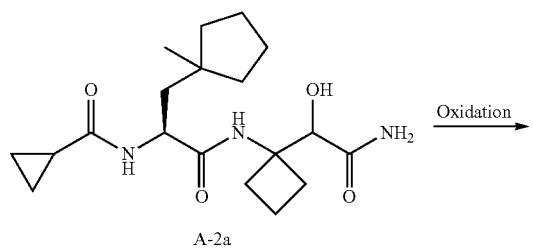

A-2a

Step a) Cyclopropanecarboxylic acid[1-[1-(carbamoyl-hydroxy-methyl)-cyclobutylcarbamoyl]-2-(1-methyl-cyclopentyl)-ethyl]-amide (A2-a)

The Boc-protected amine C4-b (40 mg, 0.1 mmol) was kept in dichloromethane containing 20% TFA/water/triisopropylsilane 9.5:0.25:0.25 (4 mL) for 2 h whereafter the solution was evaporated and the residue put under vacuum for 2 h. The afforded free amine was dissolved in DMF (4 mL) and diisopropylethylamine (0.052 mL, 0.3 mmol) was added, during stifling, followed by the addition of cyclopropanecarbonyl chloride (0.012 mL, 0.12 mmol). aq. NaHCO₃ was added and the product extracted with dichloromethane. A flash silica column in DCM-MeOH 0-10% gave the title compound (30 mg). [M+1]⁺=365.9.

Step b) Cyclopropanecarboxylic acid [1-(1-aminooxalyl-cyclobutylcarbamoyl)-2-(1-methyl-cyclopentyl)-ethyl]-amide (A2)

The α-hydroxy amide A2-a (30 mg, 0.08 mmol) was oxidized using Dess Martin periodinane as described in Ex. C5 above. The afforded crude product was purified on a prep RP HPLC-UV/MS which gave the title compound (5.7 mg). [M+1]⁺=363.9.

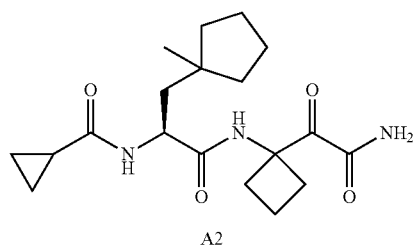

A2

EXAMPLES A3-A4

Compounds A3 and A4 in the table below were prepared according to the procedure outlined in Example A2, using the appropriate acid chloride.

TABLE A1

Ex. A3

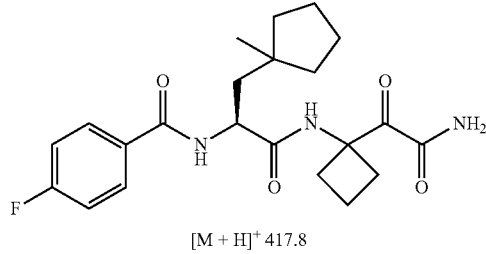 [SMILES: CC1(C[C@H](NC(=O)c2ccc(F)cc2)C(=O)NC2(C(=O)C(N)=O)CCC2)CCCC1]

[M + H]⁺ 417.8

Ex. A4

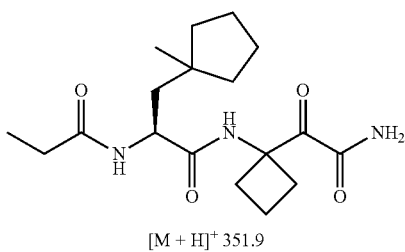 [SMILES: CCC(=O)N[C@@H](CC1(C)CCCC1)C(=O)NC1(C(=O)C(N)=O)CCC1]

[M + H]⁺ 351.9

The compounds in the table below were prepared according to the procedure outlined in Example A1, using the appropriate "P3-acid" R⁴C(=O)OH, "P1- and P2-building blocks".

TABLE A2

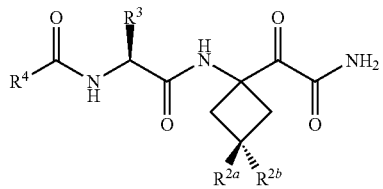

| Ex. | R⁴ | R³ | R²ᵃ | R²ᵇ | $[M+H]^+$ |
|---|---|---|---|---|---|
| A5[1] | cyclopropyl | 2,2-dimethylbutyl | F | H | 356.1 |
| A6[1] | cyclopropyl | (1-fluorocyclopentyl)methyl | H | H | 368.2 |
| A7[1,2] | 2-methylpyridin-5-yl | (1-fluorocyclopentyl)methyl | H | H | 419.2 |
| A8[1,2] | 1,1,1-trifluoro-2-hydroxypropan-2-yl | (1-fluorocyclopentyl)methyl | H | H | 440.2 |
| A9[1,2] | 2-fluoropropan-2-yl | 2,2-dimethylbutyl | F | F | 393.8 |
| A10[1,2] | 2,1-difluoroethyl | 2,2-dimethylbutyl | F | F | 397.8 |
| A11[1,2] | 2-fluoropropan-2-yl | (1-fluorocyclopentyl)methyl | F | F | 424.16 |
| A12[1,2] | 1,1-difluoroethyl | (1-fluorocyclopentyl)methyl | F | F | 428.4 |
| A13[2,3] | 2-fluoropropan-2-yl | 2,2-dimethylbutyl | H | H | 358.0 |
| A14[2,3] | 1,1,1-trifluoro-2-methylpropan-2-yl | 2,2-dimethylbutyl | H | H | 408.0 |
| A15[2,3] | 2-fluoropropan-2-yl | (1-methylcyclopentyl)methyl | H | H | 384.0 |
| A16[3,4] | 2-methylprop-2-yl | (1-fluorocyclopentyl)methyl | H | H | 384.0 |
| A17[1,5] | 2,4-difluorophenyl | (1-fluorocyclopentyl)methyl | H | H | 440.4 |
| A18[1,5] | 3,4-difluorophenyl | (1-fluorocyclopentyl)methyl | H | H | 440.2 |
| A19[1,5] | thiazol-5-yl | (1-fluorocyclopentyl)methyl | H | H | 411.3 |
| A20[1,5] | 3,5-difluorophenyl | (1-fluorocyclopentyl)methyl | H | H | 440.4 |
| A21[1,5] | 2,4,6-trifluorophenyl | (1-fluorocyclopentyl)methyl | H | H | 458.4 |
| A22[1,5] | 3,4,5-trifluorophenyl | (1-fluorocyclopentyl)methyl | H | H | 458.4 |
| A23[1,5] | 2-fluoroprop-2-yl | 1-fluorocyclopentylmethyl | H | H | 388.4 |
| A24[2] | 1,1,1-trifluoro-2-methylpropan-2-yl | 1-methylcyclopentylmethyl | H | H | 434.0 |
| A25 | 1-(trifluoromethyl)cyclopropyl | 1-fluorocyclopentylmethyl | H | H | 436.4 |
| A26 | 1-methylcyclopropyl | 1-fluorocyclopentylmethyl | H | H | 382.5 |
| A27 | 1,1,1-trifluoro-2-methylpropan-2-yl | 1-fluorocyclopentylmethyl | H | H | 438.4 |
| A28 | 1-(trifluoromethyl)cyclobutyl | 1-fluorocyclopentylmethyl | H | H | 450.4 |
| A29 | 1,1,1-trifluoro-2-methylpropan-2-yl | 1-methylcyclopentylmethyl | F | H | 454.3 |
| A30 | 2-fluoropropan-2-yl | 1-fluorocyclopentylmethyl | F | H | 406.6 |
| A31 | 2-fluoropropan-2-yl | 1-methyl-cyclopentylmethyl | F | F | 420.5 |
| A32 | 1,1,difluoro-ethyl | 1-methylcyclopentylmethyl | F | F | 424.5 |
| A33 | 1,1-difluoroethyl | 1-fluorocyclopentylmethyl | H | H | 392.0 |
| A34 | pyridin-2-yl | 1-fluorocyclopentylmethyl | H | H | 405.0 |

[1]Removal of the Boc-group in step b was performed using 4M HCl in dioxane.
[2]Oxidation of the α-hydroxy amide to the Corr. α-keto amide was performed using DMSO-method described in Ex. C8.
[3]Removal of the Boc-group in step b was performed with TFA in DCM.
[4]Oxidation of the α-hydroxy amide to the Corr. α-keto amide was performed using Dess Martin periodinane as described in Ex. C1.
[5]Oxidation of the α-hydroxy amide to the Corr. α-keto amide was performed by treating a solution of the alcohol with a 15% solution of Dess-Martin periodinane in DCM.

The compounds in Table A3 below were prepared according to the procedure described in Ex. A1, using the appropriate "P3-acid" R⁴C(=O)OH and "P1- and P2-building" blocks, and finally oxidized using Dess Martin periodinane.

TABLE A3

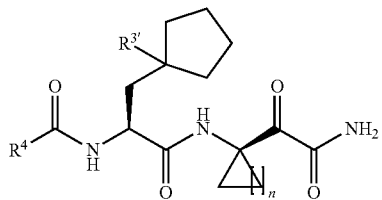

| Ex. | R⁴ | R³' | n | $[M+H]^+$ |
|---|---|---|---|---|
| A35[4] | cyclopropyl | F | 3 | 382.08 |
| A36[4] | 1,1,1-trifluoro-2-methylpropan-2-yl | F | 3 | 451.9 |
| A37[4] | 3-methyloxetan-3-yl | F | 3 | 411.9 |
| A38 | 1-(trifluoromethyl)cyclopropyl | F | 1 | 422.4 |
| A39 | 1,1,1-trifluoro-2-methylpropan-2-yl | F | 1 | 424.4 |
| A40 | 1-(trifluoromethyl)cyclopropyl | CH₃ | 1 | 418.3 |
| A41[2] | 3-methyloxetan-3-yl | CH₃ | 1 | 380.1 |

[2]Oxidation of the α-hydroxy amide to the Corr. α-keto amide was performed using the DMSO-method described in Ex. C8.
[4]Oxidation of the α-hydroxy amide to the Corr. α-keto amide was performed using Dess Martin periodinane as described in Ex. C1.

EXAMPLE A42

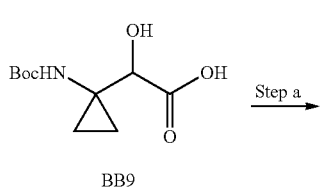

BB9    Step a

49

-continued

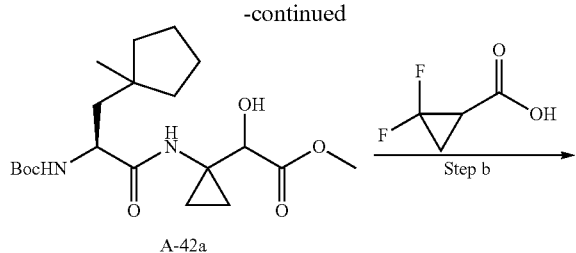
A-42a

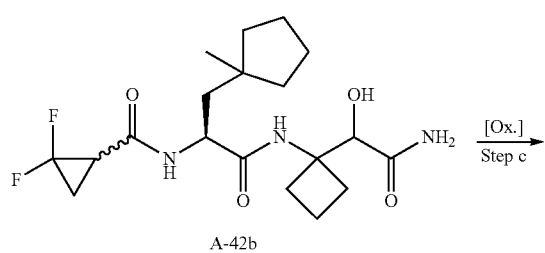
A-42b

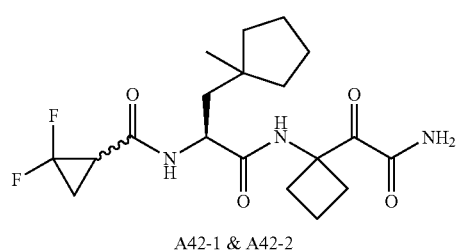
A42-1 & A42-2

Step a) methyl 2-(1-((S)-2-((tert-butoxycarbonyl)amino)-3-(1-methylcyclopentyl)propanamido)cyclopropyl)-2-hydroxyacetate (A42-a)

The hydroxyl acid BB8 (100 mg, 0.43 mmol, 1 eq.) was dissolved in methanol (10 mL) and TSM-CH$_2$N$_2$ (2M in hexanes) was added until the yellow colour remained and TLC showed no reaming starting material. The solvent was removed under vacuum. The remaining solid was dissolved in methanol: acetic chloride (9:1) and resulting mixture was stirred at room temperature over night. The solvent was removed under vacuum. The residue was dissolved in DMF (5 mL), and 2-tert-Butoxycarbonylamino-3-(1-methyl-cyclopentyl)-propionic acid (1 eq.) and diisopropylethylamine (4 eq.) was added. Thereafter HATU (1 eq.) was added and the resulting reaction mixture stirred at room temperature for 1.5 hours. The solvent was removed under vacuum and the crude product was purified on silica column using hexane:EtOAc (3:3 to 1:1) as eluent which gave the title compound (38%).

Step b) N-((2S)-1-((1-(2-amino-1-hydroxy-2-oxoethyl)cyclobutyl)amino)-3-(1-methylcyclopentyl)-1-oxopropan-2-yl)-2,2-difluorocyclopropanecarboxamide (A42-b)

Methyl 2-(14(S)-2-((tert-butoxycarbonyl)amino)-3-(1 methylcyclopentyl)-propanamido)cyclopropyl)-2-hydroxyacetate was dissolved in methanol: acetic chloride (9:1) and resulting mixture was stirred at room temperature over night. The solvent was removed under vacuum. The residue was dissolved in DMF (5 mL), and 2,2-difluorocyclopropanecarboxylic acid (1 eq) and diisopropylethylamine (4 eq) was added. Thereafter HATU (1 eq) was added and the resulting reaction mixture stirred at room temperature for 1.5 hours. The solvent was removed under vacuum and the crude product was dissolve in EtOAc and washed with NaHCO3 (aq), HCL (1.2 M) and H$_2$O. The organic phase was concentrated under vacuum and the residue was dissolve in methanol. The mixture was cooled to 0° C. and NH$_3$ bubbled thru the reaction mixture. The solvent was evaporated and the crude product used in next step.

N—((S)-1-((1-(2-amino-2-oxoacetyl)cyclopropyl)amino)-3-(1-methylcyclopentyl)-1-oxopropan-2-yl)-2,2-difluorocyclopropanecarboxamide Step c) (S)—N-(1-((1-(2-amino-2-oxoacetyl)cyclobutyl)amino)-3-(1-methylcyclopentyl)-1-oxopropan-2-yl)cyclopropanecarboxamide A42-1 & A42-2

A solution of Dess-Martin periodinane (1.5 eq) in dichloroethane (4 mL) was added to the solid α-hydroxy amide A42-b. The mixture was stirred for 1 h and then NaHCO$_3$ (aq) was added. The organic layer was separated and concentrated. Purification on prep RP HPLC-UV/MS gave the title compound as two separated diastereomers. [M+1]$^+$386.3 and. [M+1]$^+$386.3.

The below compounds were prepared according to the method described in Example A42, using the appropriate building blocks.

| Ex. A43-1 & A43-2 | 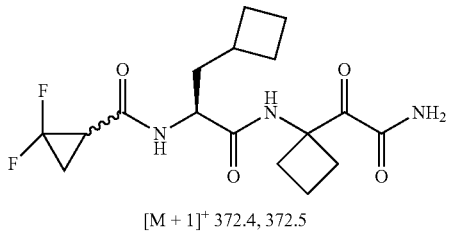 [M + 1]$^+$ 372.4, 372.5 |
|---|---|
| Ex. A44-1 & A44-2 | 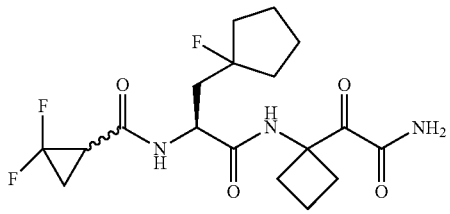 [M + 1]$^+$ 390.4, 390.4 |

The compounds in the table below were prepared according to the procedure outlined in Example A1, using the appropriate "P3-acid" R$^4$C(=O)OH, "P1- and P2-building blocks".

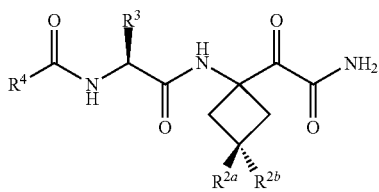

| Ex. | R⁴ | R³ | R²ᵃ | R²ᵇ | [M + H]⁺ |
|---|---|---|---|---|---|
| A45 | 1,1-difluoroethyl | 1-fluorocyclopentylmethyl | F | H | 410.3 |
| A46 | 1,1-difluoroethyl | 1-methylcyclopentylmethyl | F | H | 406.4 |
| A47 | 3-methylpyridin-2-yl | 1-fluorocyclopentylmethyl | H | H | 419.4 |
| A48 | 2-fluoropropan-2-yl | 1-fluorocyclopentylmethyl | F | H | 402.4 |
| A49¹ | 1,1,1,trifluoro-2-methylpropan-2-yl | 1-fluorocyclopentylmethyl | OMe | H | 468.6 |
| A50¹ | 1,1-difluoroethyl | 1-fluorocyclopentylmethyl | OMe | H | |
| A51¹ | 2-fluoropropan-2-yl | 1-fluorocyclopentylmethyl | OMe | H | |

¹Removal of the Boc-group in steps a and b was performed using conc. HCl:dioxane 1:3.

EXAMPLE U1

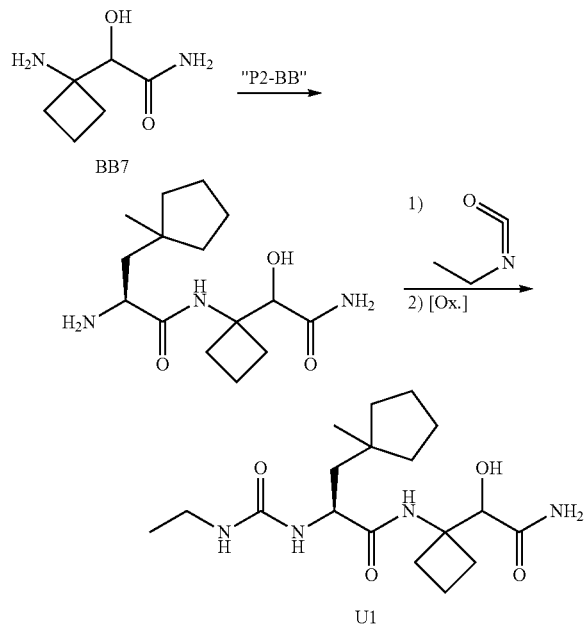

(S)—N-(1-(2-amino-2-oxoacetyl)cyclobutyl)-2-(3-ethylureido)-3-(1-methylcyclopentyl)-propanamide (U1)

The amine BB7 was coupled to the "P2-building block (S)-2-((tert-butoxycarbonyl)amino)-3-(1-methylcyclopentyl)propanoic acid according to the method described in Ex. C1 step b. The afforded amine (160 mg, 0.4 mmol) was kept in dichloromethane containing 20% TFA/water/triisopropylsilane 9.5:0.25:0.25 (8 mL) for 2 h whereafter the solution was evaporated and the residue put under vacuum for 2 h. The afforded free amine was dissolved in DMF (15 mL) and diisopropylethylamine (0.21 mL, 1.2 mmol) was added, during stifling, followed by the addition of ethlyisocyanate (0.4 mmol, 0.032 mL). aq. NaHCO₃ was added and the product extracted with dichloromethane. A flash silica column in DCM-MeOH 0-10% gave a residue to which was added to a solution of Dess-Martin periodinane (200 mg, 0.47 mmol) in dichloroethane. After stirring for 2 h the solution was washed with aq. NaHCO₃, concentrated to dryness and purified on a prep. HPLC-UV/MS which gave 24 mg of the title compound. [M+1]⁺=367.1.

Biological Examples

Determination of Cathepsin K Proteolytic Catalytic Activity

Convenient assays for cathepsin K are carried out using human recombinant enzyme, such as that described in PDB. ID BC016058 standard; mRNA; HUM; 1699 BP.

DE *Homo sapiens* cathepsin K (pycnodysostosis), mRNA (cDNA clone MGC:23107
RX MEDLINE;. RX PUBMED; 12477932.
DR RZPD; IRALp962G1234.
DR SWISS-PROT; P43235;

The recombinant cathepsin K can be expressed in a variety of commercially available expression systems including *E coli, Pichia* and Baculovirus systems. The purified enzyme is activated by removal of the prosequence by conventional methods.

Standard assay conditions for the determination of kinetic constants used a fluorogenic peptide substrate, typically H-D-Ala-Leu-Lys-AMC, and were determined in either 100 mM Mes/Tris, pH 7.0 containing 1 mM EDTA and 10 mM 2-mercaptoethanol or 100 mMNa phosphate, imM EDTA, 0.1% PEG4000 pH 6.5 or 100 mM Na acetate, pH 5.5 containing 5 mM EDTA and 20 mM cysteine, in each case optionally with 1M DTT as stabiliser. The enzyme concentration used was 5 nM. The stock substrate solution was prepared at 10 mM in DMSO. Screens were carried out at a fixed substrate concentration of 60 µM and detailed kinetic studies with doubling dilutions of substrate from 250 µM. The total DMSO concentration in the assay was kept below 3%. All assays were conducted at ambient temperature. Product fluorescence (excitation at 390 nm, emission at 460 nm) was monitored with a Labsystems Fluoroskan Ascent fluorescent plate reader. Product progress curves were generated over 15 minutes following generation of AMC product.

Cathepsin S Ki Determination

The assay uses baculovirus-expressed human cathepsin S and the boc-Val-Leu-Lys-AMC fluorescent substrate available from Bachem in a 384 well plate format, in which 7 test compounds can be tested in parallel with a positive control comprising a known cathepsin S inhibitor comparator.

Substrate Dilutions

280 µL/well of 12.5% DMSO are added to rows B-H of two columns of a 96 deep well polypropylene plate. 70 µL/well of substrate is added to row A. 2×250 µL/well of assay buffer (100 mM Na phosphate, 100 mM NaCl, pH 6.5) is added to row A, mixed, and double diluted down the plate to row H.
Inhibitor Dilutions 100 µL/well of assay buffer is added to columns 2-5 and 7-12 of 4 rows of a 96 well V bottom polypropylene plate. 200 µL/well of assay buffer is added to columns 1 and 6.

The first test compound prepared in DMSO is added to column 1 of the top row, typically at a volume to provide between 10 and 30 times the initially determined rough $K_i$. The rough $K_i$ is calculated from a preliminary run in which 10 µL/well of 1 mM boc-VLK-AMC (1/10 dilution of 10 mM stock in DMSO diluted into assay buffer) is dispensed to rows B to H and 20 µl/well to row A of a 96 well Microfluor™ plate. 2 µl of each 10 mM test compound is added to a separate well on row A, columns 1-10. Add 90 µl assay buffer containing 1 mM DTT and 2 nM cathepsin S to each well of rows B-H and 180 µl to row A. Mix row A using a multichannel pipette and double dilute to row G. Mix row H and read in the fluorescent spectrophotometer. The readings are Prism data fitted to the competitive inhibition equation, setting S=100 µM and $K_M$=100 µM to obtain an estimate of the up to a maximum of 100 µM.

The second test compound is added to column 6 of the top row, the third to column 1 of the second row etc. Add 1 µL of comparator to column 6 of the bottom row. Mix column 1 and double dilute to column 5. Mix column 6 and double dilute to column 10.

Using an 8-channel multistepping pipette set to 5×10 µL, distribute 10 µL/well of substrate to the 384 well assay plate. Distribute the first column of the substrate dilution plate to all columns of the assay plate starting at row A. The tip spacing of the multichannel pipette will correctly skip alternate rows. Distribute the second column to all columns starting at row B.

Using a 12-channel multistepping pipette set to 4×10 µL, distribute 10 µL/well of inhibitor to the 384 well assay plate. Distribute the first row of the inhibitor dilution plate to alternate rows of the assay plate starting at A1. The tip spacing of the multichannel pipette will correctly skip alternate columns. Similarly, distribute the second, third and fourth rows to alternate rows and columns starting at A2, B1 and B2 respectively.

Mix 20 mL assay buffer and 20 µL 1M DTT. Add sufficient cathepsin S to give 2 nM final concentration.

Using the a distributor such as a Multidrop 384, add 30 µL/well to all wells of the assay plate and read in fluorescent spectrophotometer such as an Ascent.

Fluorescent readings, (excitation and emission wavelengths 390 nm and 460 nm respectively, set using bandpass filters) reflecting the extent of enzyme cleavage of the fluorescent substrate, notwithstanding the inhibitor, are linear rate fitted for each well.

Fitted rates for all wells for each inhibitor are fitted to the competitive inhibition equation using SigmaPlot 2000 to determine V, Km and Ki values.
Cathepsin L Ki The procedure above with the following amendments is used for the determination of Ki for cathepsin L.

The enzyme is commercially available human cathepsin L (for example Calbiochem). The substrate is H-D-Val-Leu-Lys-AMC available from Bahcem. The assay buffer is 100 mM sodium acetate 1 mM EDTA, pH5.5) The DMSO stock (10 mM in 100% DMSO) is diluted to 10% in assay buffer. Enzyme is prepared at 5 nM concentration in assay buffer plus 1 mM dithiothreitol just before use. 2 µL of 10 mM inhibitor made up in 100% DMSO is dispensed into row A. 10 µL of 50 µM substrate (=1/200 dilution of 10 mM stock in DMSO, diluted in assay buffer).

Inhibition Studies

Potential inhibitors are screened using the above assay with variable concentrations of test compound. Reactions were initiated by addition of enzyme to buffered solutions of substrate and inhibitor. $K_i$ values were calculated according to equation 1.

$$v_0 = \frac{VS}{K_M\left(1 + \frac{I}{K_i}\right) + S} \quad (1)$$

where $v_0$ is the velocity of the reaction, V is the maximal velocity, S is the concentration of substrate with Michaelis constant of $K_M$, and I is the concentration of inhibitor.

The inhibition of cathepsin S, cathepsin K and cathepsin L exhibited by a selection of the compounds of the invention represented as Ki values is presented in Table 1.

TABLE 1

| Example | Ki Cat. S | Ki Cat. K | Ki Cat. L |
|---------|-----------|-----------|-----------|
| C1      | 12        | 770       | 11000     |
| C2      | 8.3       | 510       | 9700      |
| C3      | 1.3       | 440       | 1700      |
| C4      | 1.1       | 720       | 1700      |
| C5      | 2.8       | 1100      | 5300      |
| C6      | 2.4       | 960       | 3700      |
| C7      | 6.4       | 2500      | 21000     |
| C9      | 4.6       | 2100      | 520       |
| C11     | 3.7       | 1200      | 2600      |
| C12     | 2.7       | 1900      | 3200      |
| C14     | 2.1       | 640       | 2800      |
| A1      | 0.084     | 500       | 230       |
| A2      | 0.3       | 630       | 1800      |
| A3      | 0.1       | 140       | 180       |
| A4      | 4.9       | 2300      | 12000     |
| A7      | 0.88      | 650       | 260       |
| A13     | 19        | 220       | 4300      |
| A17     | 0.67      | 490       | 490       |
| A24     | 1.2       | 300       | 3000      |
| A25     | 3.6       | 1300      | 14000     |
| A28     | 31        | 15000     | 23000     |
| A31     | 2.3       | 990       | 11000     |
| A34     | 0.77      | 180       | 710       |
| A35     | 9.7       | 7500      | 18000     |
| A38     | 7.6       | 4600      | >200000   |
| A43-1   | 1.3       | 280       | 4200      |

The compounds of formula I are thus potent inhibitors of cathepsin S and yet selective over the closely related cathepsin K and L.
Permeability This experiment measures transport of inhibitors through the cells of the human gastroenteric canal. The assay uses the well known Caco-2 cells with a passage number between 40 and 60.
Apical to Basolateral Transport Generally every compound will be tested in 2-4 wells. The basolateral and the apical wells will contain 1.5 mL and 0.4 mL transport buffer (TB), respectively, and the standard concentration of the tested substances is 10 µM. Furthermore all test solutions and buffers will contain 1% DMSO. Prior to the experiment the transport plates are pre-coated with culture medium containing 10% serum for 30 minutes to avoid non-specific binding to plastic material. After 21 to 28 days in culture on filter supports, the cells are ready for permeability experiments.

Transport plate no 1 comprises 3 rows of 4 wells each. Row 1 is denoted Wash, row 2 "30 minutes" and row 3 "60 minutes". Transport plate no 2 comprises 3 rows of 4 wells, one denoted row 4 "90 minutes", row 5 "120 minutes and the remaining row unassigned.

The culture medium from the apical wells is removed and the inserts are transferred to a wash row (No. 1) in a transport plate (plate no. 1) out of 2 plates without inserts, which have already been prepared with 1.5 mL transport buffer (HBSS, 25 mM HEPES, pH 7.4) in rows 1 to 5. In A→B screening the TB in basolateral well also contains 1% Bovine Serum Albumin 0.5 mL transport buffer (HBSS, 25 mM MES, pH 6.5) is added to the inserts and the cell monolayers equilibrated in the transport buffer system for 30 minutes at 37° C. in a polymix shaker. After being equilibrated to the buffer system the Transepithelial electrical resistance value (TEER) is measured in each well by an EVOM chop stick instrument. The TEER values are usually between 400 to 1000Ω per well (depends on passage number used).

The transport buffer (TB, pH 6.5) is removed from the apical side and the insert is transferred to the 30 minutes row (No. 2) and fresh 425 μL TB (pH 6.5), including the test substance is added to the apical (donor) well. The plates are incubated in a polymix shaker at 37° C. with a low shaking velocity of approximately 150 to 300 rpm.

After 30 minutes incubation in row 2, the inserts are moved to new pre-warmed basolateral (receiver) wells every 30 minutes; row 3 (60 minutes), 4 (90 minutes) and 5 (120 minutes).

25 μL samples are taken from the apical solution after ~2 minutes and at the end of the experiment. These samples represent donor samples from the start and the end of the experiment.

300 μL will be taken from the basolateral (receiver) wells at each scheduled time point and the post value of TEER is measured at the end the experiment. To all collected samples acetonitrile will be added to a final concentration of 50% in the samples. The collected samples will be stored at −20° C. until analysis by HPLC or LC-MS.

Basolateral to Apical Transport

Generally every compound will be tested in 2-4 wells. The basolateral and the apical wells will contain 1.55 mL and 0.4 mL TB, respectively, and the standard concentration of the tested substances is 10 μM. Furthermore all test solutions and buffers will contain 1% DMSO. Prior to the experiment the transport plates are precoated with culture medium containing 10% serum for 30 minutes to avoid nonspecific binding to plastic material.

After 21 to 28 days in culture on filter supports the cells are ready for permeability experiments. The culture medium from the apical wells are removed and the inserts are transferred to a wash row (No. 1) in a new plate without inserts (Transport plate).

The transport plate comprises 3 rows of 4 wells. Row 1 is denoted "wash" and row 3 is the "experimental row". The transport plate has previously been prepared with 1.5 mL TB (pH 7.4) in wash row No. 1 and with 1.55 mL TB (pH 7.4), including the test substance, in experimental row No. 3 (donor side).

0.5 mL transport buffer (HBSS, 25 mM MES, pH 6.5) is added to the inserts in row No. 1 and the cell monolayers are equilibrated in the transport buffer system for 30 minutes, 37° C. in a polymix shaker. After being equilibrated to the buffer system the TEER value is measured in each well by an EVOM chop stick instrument.

The transport buffer (TB, pH 6.5) is removed from the apical side and the insert is transferred to row 3 and 400 μL fresh TB, pH 6.5 is added to the inserts. After 30 minutes 250 μL is withdrawn from the apical (receiver) well and replaced by fresh transport buffer. Thereafter 250 μL samples will be withdrawn and replaced by fresh transport buffer every 30 minutes until the end of the experiment at 120 minutes, and finally a post value of TEER is measured at the end of the experiment. A 25 μL samples will be taken from the basolateral (donor) compartment after ~2 minutes and at the end of the experiment. These samples represent donor samples from the start and the end of the experiment.

To all collected samples acetonitrile will be added to a final concentration of 50% in the samples. The collected samples will be stored at −20° C. until analysis by HPLC or LC-MS.

Calculation

Determination of the cumulative fraction absorbed, $FA_{cum}$, versus time. $FA_{cum}$ is calculated from:

$$FA_{cum} = \sum \frac{C_{RI}}{C_{DI}}$$

Where $C_{Ri}$ is the receiver concentration at the end of the interval i and $C_{Di}$ is the donor concentration at the beginning of interval i. A linear relationship should be obtained.

The determination of permeability coefficients ($P_{app}$, cm/s) are calculated from:

$$P_{app} = \frac{(k \cdot V_R)}{(A \cdot 60)}$$

where k is the transport rate ($min^{-1}$) defined as the slope obtained by linear regression of cumulative fraction absorbed ($FA_{cum}$) as a function of time (min), $V_R$ is the volume in the receiver chamber (mL), and A is the area of the filter ($cm^2$).

Reference Compounds

| Category of absorption in man | Markers | absorption in man (%) |
| --- | --- | --- |
| PASSIVE TRANSPORT | | |
| Low (0-20%) | Mannitol | 16 |
| | Methotrexate | 20 |
| Moderate (21-75%) | Acyclovir | 30 |
| High (76-100%) | Propranolol | 90 |
| | Caffeine | 100 |
| ACTIVE TRANSPORT | | |
| Amino acid transporter | L-Phenylalanine | 100 |
| ACTIVE EFFLUX | | |
| PGP-MDR1 | Digoxin | 30 |

Greater permeability through the gastrointestinal tissue is advantageous in that it allows for the use of a smaller dose to achieve similar levels of exposure to a less permeable compound administered in a higher dose. A low dose is advantageous in that it minimizes the cost of goods for a daily dose, which is a crucial parameter in a drug which is taken for protracted time periods.

All references referred to in this application, including patent and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:

1. A compound of the formula I:

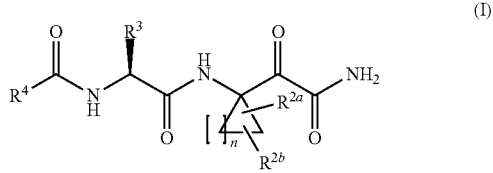

(I)

wherein $R^{2a}$ and $R^{2b}$ are independently selected from H, halo, $C_1$-$C_4$alkyl, $C_1$-$C_4$haloalkyl, $C_1$-$C_4$alkoxy, or $R^{2a}$ and $R^{2b}$ together with the carbon atom to which they are attached to form a $C_3$-$C_6$cycloalkyl;

$R^3$ is a $C_5$-$C_{10}$ alkyl, optionally substituted with 1-3 substituents independently selected from halo, $C_1$-$C_4$haloalkyl, $C_1$-$C_4$alkoxy, $C_1$-$C_4$haloalkoxy; or $R^3$ is a $C_2$-$C_4$alkyl chain with at least 2 chloro or 3 flouro substituents; or $R^3$ is $C_3$-$C_7$cycloalkylmethyl, optionally substituted with 1-3 substituents independently selected from $C_1$-$C_4$alkyl, halo, $C_1$-$C_4$haloalkyl, $C_1$-$C_4$alkoxy, $C_1$-$C_4$haloalkoxy;

$R^4$ is $C_1$-$C_6$alkyl, $C_1$-$C_6$haloalkyl, $C_1$-$C_6$alkoxy, $C_1$-$C_6$haloalkoxy, $C_1$-$C_6$alkylamino, $C_1$-$C_6$dialylamino;

n is 1, 2 or 3; and

Ra and Rb are independently H, $C_1$-$C_4$alkyl;

or a pharmaceutically acceptable salt, hydrate or N-oxide thereof.

2. A compound according to claim 1, wherein $R^{2a}$ and $R^{2b}$ are both H.

3. A compound according to claim 1, wherein n is 2 and $R^{2a}$ and $R^{2b}$ are both F.

4. A compound according to claim 1, wherein n is 2, one of $R^{2a}$ and $R^{2b}$ is H and the other is Cl, F, $F_3C$ or MeO.

5. A compound according to claim 1, wherein $R^3$ is t-butylmethyl, cyclobutylmethyl, 1-methylcyclobutylmethyl or 1-methylcyclopentylmethyl, any of which is optionally substituted with on or two F or $CH_3O$.

6. A compound according to claim 1, wherein $R^3$ is 1-metylcyclopentylmethyl or 1-fluorocyclopentylmethyl.

7. A compound according to claim 1, wherein $R^4$ is $C_1$-$C_6$alkyl or mono, di or triflouro$C_1$-$C_6$alkyl.

8. A compound according to claim 1, having the formula II:

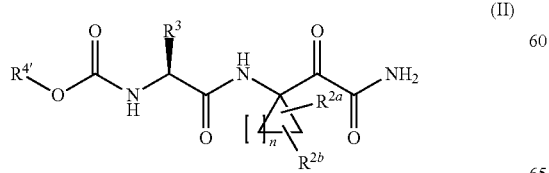

(II)

wherein $R^{4'}$ is $C_1$-$C_6$alkyl or $C_1$-$C_6$haloalkyl.

9. A compound according to claim 8, wherein $R^{4'}$ is methyl, ethyl or tert.butyl.

10. A compound according to claim 1, wherein n is 1 or 2.

11. A compound according to claim 1, having the formula III:

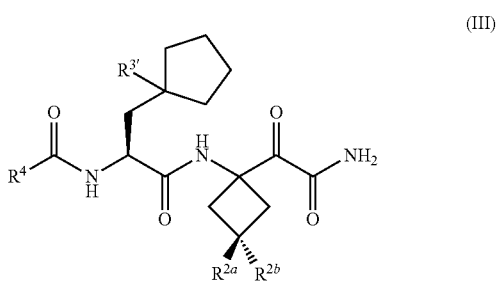

(III)

wherein $R^{3'}$ is $CH_3$ or F, $R^{2a}$ and $R^{2b}$ are independently H or F, and $R^4$ is $C_1$-$C_6$alkyl, or $C_1$-$C_6$haloalkyl.

12. A pharmaceutical composition comprising a compound according to claim 1 and pharmaceutically acceptable vehicle therefor.

13. A method for the treatment of a disorder comprising administrating an effective amount of a compound as defined in claim 1 to a human or animal afflicted with or at risk of the disorder, wherein the disorder is rheumatoid arthritis (RA), multiple sclerosis (MS), myasthenia gravis (MG), Sjögrens syndrome, asthma, atherosclerosis, chronic obstructive pulmonary disease (COPD) and neuropathic pain.

14. A compound having the structure

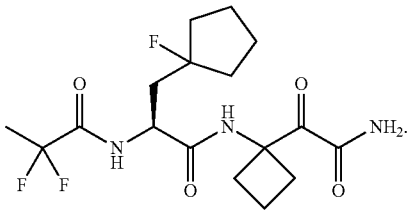 [SMILES: CC(F)(F)C(=O)N[C@@H](CC1(F)CCCC1)C(=O)NC1(C(=O)C(N)=O)CCC1]

15. A method for the treatment of a disorder comprising administrating an effective amount of a compound as defined in claim 14 to a human or animal afflicted with or at risk of the disorder, wherein the disorder is neuropathic pain.

16. The compound according to claim 6, wherein $R^3$ is 1-flourocyclopentylmethyl.

17. The compound according to claim 10, wherein n is 2.

18. A compound having the structure

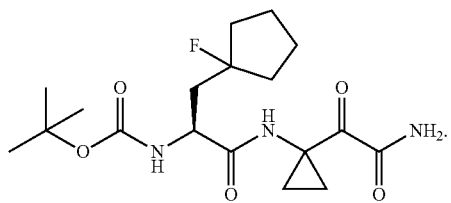 [SMILES: CC(C)(C)OC(=O)N[C@@H](CC1(F)CCCC1)C(=O)NC1(C(=O)C(N)=O)CC1]

19. A compound having the structure

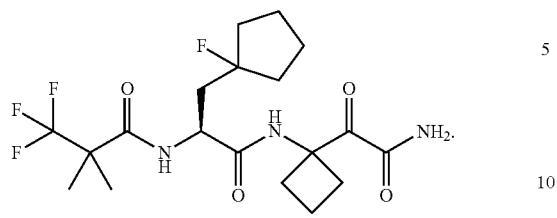

20. A method for the treatment of a disorder comprising administrating an effective amount of the compound of claim 18 to a human or animal afflicted with or at risk of a disorder, wherein the disorder is neuropathic pain.

21. A method for the treatment of a disorder comprising administrating an effect amount of a compound as defined in claim 19 to a human or animal afflicted with or at risk of a disorder, wherein the disorder is neuropathic pain.

22. A method according to claim 13, wherein the disorder is neuropathic pain.

* * * * *